(12) United States Patent
Woehr et al.

(10) Patent No.: US 8,376,994 B2
(45) Date of Patent: *Feb. 19, 2013

(54) PROTECTIVE DEVICE FOR AN INJECTION NEEDLE

(75) Inventors: Kevin Woehr, Felsberg (DE); Juergen Fuchs, Bad Emstal (DE); Kenneth C. Raines, Bethlehem, PA (US); Joel M. Bartholomew, Danielsvile, PA (US)

(73) Assignee: B. Braun Melsungen AG, Melsungen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/099,945

(22) Filed: May 3, 2011

(65) Prior Publication Data
US 2011/0208133 A1 Aug. 25, 2011

Related U.S. Application Data

(60) Continuation of application No. 12/574,963, filed on Oct. 7, 2009, now Pat. No. 8,100,858, which is a continuation of application No. 11/537,368, filed on Sep. 29, 2006, now Pat. No. 7,611,487, which is a division of application No. 10/856,315, filed on May (Continued)

(30) Foreign Application Priority Data

Feb. 26, 2001 (DE) .................... 201 3 363

(51) Int. Cl.
*A61M 5/00* (2006.01)
*A61M 5/178* (2006.01)
*A61M 5/32* (2006.01)
(52) U.S. Cl. .................... 604/110; 604/198; 604/164.08

(58) Field of Classification Search ............... 604/93.01, 604/158–167.05, 174–180, 263, 110, 192–198
See application file for complete search history.

(56) References Cited

U.S. PATENT DOCUMENTS

| 3,610,240 A | 10/1971 | Harautuneian |
| 3,904,033 A | 9/1975 | Haerr |

(Continued)

FOREIGN PATENT DOCUMENTS

| EP | 0 352 928 B1 | 12/1992 |
| EP | 0 554 841 A1 | 8/1993 |

(Continued)

OTHER PUBLICATIONS

Decision on Opposition by Terumo Corporation; In the Court of the Commissioner of Patents for the Australian Patent Office; Patent Application No. 2006200679 in the name of B. Braun Melsungen AG; *Terumo Corporation v. B. Braun Melsunqen AG* [2011] APO 71 dated Sep. 16, 2011 (17 pages).

(Continued)

*Primary Examiner* — Matthew F Desanto
(74) *Attorney, Agent, or Firm* — Klein, O'Neill & Singh, LLP

(57) ABSTRACT

Protective devices for injection needles or infusion needles that include a needle holder at a proximal end of the needle, on whose shaft a protective element for the needle tip can be positioned and moved, are herein disclosed. The protective element is configured to block the needle tip following an injection to prevent accidental contact therewith. The protective element may be positioned on the shaft in a ready to use position inside a grip part or middle retaining portion, which is also used to activate the protective element over the needle following the injection.

15 Claims, 10 Drawing Sheets

Related U.S. Application Data 27, 2004, now Pat. No. 7,125,397, which is a continuation-in-part of application No. 10/468,923, filed as application No. PCT/EP02/02042 on Feb. 26, 2002, now Pat. No. 7,214,211.

(56) References Cited

U.S. PATENT DOCUMENTS

| | | | |
|---|---|---|---|
| 4,160,450 A | 7/1979 | Doherty | |
| 4,250,881 A | 2/1981 | Smith | |
| 4,383,530 A * | 5/1983 | Bruno | 604/274 |
| 4,725,267 A | 2/1988 | Vaillancourt | |
| 4,735,618 A | 4/1988 | Hagen | |
| 4,747,831 A | 5/1988 | Kulli | |
| 4,790,828 A | 12/1988 | Dombrowski et al. | |
| 4,795,432 A | 1/1989 | Karczmer | |
| 4,846,809 A | 7/1989 | Sims | |
| 4,929,241 A | 5/1990 | Kulli | |
| 4,944,725 A | 7/1990 | McDonald | |
| 4,952,207 A | 8/1990 | Lemieux | |
| 4,964,854 A | 10/1990 | Luther | |
| 4,978,344 A | 12/1990 | Dombrowski et al. | |
| 4,994,041 A | 2/1991 | Dombrowski et al. | |
| 5,049,136 A | 9/1991 | Johnson | |
| 5,051,109 A | 9/1991 | Simon | |
| 5,053,017 A | 10/1991 | Chamuel | |
| 5,053,107 A | 10/1991 | Barber, Jr. | |
| 5,085,648 A | 2/1992 | Purdy et al. | |
| 5,120,320 A | 6/1992 | Fayngold | |
| 5,120,321 A | 6/1992 | Oksman et al. | |
| 5,126,090 A | 6/1992 | Egolf et al. | |
| 5,135,504 A | 8/1992 | McLees | |
| 5,147,327 A | 9/1992 | Johnson | |
| 5,171,229 A | 12/1992 | McNeil et al. | |
| 5,183,468 A | 2/1993 | McLees | |
| 5,215,525 A | 6/1993 | Sturman | |
| 5,215,528 A | 6/1993 | Purdy et al. | |
| 5,217,438 A | 6/1993 | Davis et al. | |
| RE34,416 E | 10/1993 | Lemieux | |
| 5,279,570 A | 1/1994 | Dombrowski et al. | |
| 5,279,591 A | 1/1994 | Simon | |
| 5,300,045 A | 4/1994 | Plassche, Jr. | |
| 5,312,371 A | 5/1994 | Dombrowski et al. | |
| 5,322,517 A | 6/1994 | Sircom et al. | |
| 5,328,482 A | 7/1994 | Sircom et al. | |
| 5,334,158 A | 8/1994 | McLees | |
| 5,344,408 A | 9/1994 | Partika | |
| 5,348,544 A | 9/1994 | Sweeney et al. | |
| 5,370,623 A | 12/1994 | Kreamer | |
| 5,419,766 A | 5/1995 | Chang et al. | |
| 5,423,766 A | 6/1995 | Di Cesare | |
| 5,458,658 A | 10/1995 | Sircom | |
| 5,501,675 A | 3/1996 | Erskine | |
| 5,549,570 A | 8/1996 | Rogalsky | |
| 5,558,651 A | 9/1996 | Crawford et al. | |
| 5,584,809 A | 12/1996 | Gaba | |
| 5,584,810 A | 12/1996 | Brimhall | |
| 5,584,818 A | 12/1996 | Morrison | |
| 5,599,310 A | 2/1997 | Bogert | |
| 5,601,536 A | 2/1997 | Crawford et al. | |
| 5,611,781 A | 3/1997 | Sircom et al. | |
| 5,662,610 A | 9/1997 | Sircom | |
| 5,697,907 A | 12/1997 | Gaba | |
| 5,718,688 A | 2/1998 | Wozencroft | |
| 5,738,665 A | 4/1998 | Caizza et al. | |
| 5,843,048 A | 12/1998 | Gross | |
| 5,879,337 A | 3/1999 | Kuracina et al. | |
| 5,882,337 A | 3/1999 | Bogert et al. | |
| 6,001,080 A | 12/1999 | Kuracina et al. | |
| 6,004,294 A | 12/1999 | Brimhall et al. | |
| 6,117,108 A | 9/2000 | Woehr et al. | |
| 6,224,569 B1 | 5/2001 | Brimhall | |
| 6,287,278 B1 | 9/2001 | Woehr et al. | |
| 6,443,929 B1 | 9/2002 | Kuracina et al. | |
| 6,616,630 B1 | 9/2003 | Woehr et al. | |
| 6,652,486 B2 | 11/2003 | Bialecki et al. | |
| 6,749,588 B1 | 6/2004 | Howell et al. | |

FOREIGN PATENT DOCUMENTS

| | | |
|---|---|---|
| EP | 0 588 470 A1 | 3/1994 |
| EP | 0 750 915 A2 | 1/1997 |
| EP | 0 750 916 A2 | 1/1997 |
| EP | 0 747 085 B2 | 4/2003 |
| EP | 1 003 588 B1 | 11/2004 |
| EP | 1 180 381 B1 | 12/2005 |
| JP | 9-99068 | 4/1997 |
| JP | 9-99073 | 4/1997 |
| MX | 209311 | 10/1997 |
| WO | WO 90/08564 | 8/1990 |
| WO | WO 97/42989 | 11/1997 |
| WO | WO 99/08742 | 2/1999 |
| WO | WO 00/69501 | 11/2000 |

OTHER PUBLICATIONS

Hoffer, Erik K. et al., "Peripherally Inserted Central Catheters with Distal versus Proximal Valves: Prospective Randomized Trial", Journal of Vascular and Interventional Radiology, Oct. 2001, pp. 1173-1177, vol. 12 No. 10 (5 pages).

Imager™ II Angiographic Catheter, product information. Boston Scientific Online www.bostonscientific.com (3 sheets).

Information Sheet on Multilumen CVPs. www.icufaqs.org/Central-Lines and www.cc.nih.gov/vads/lines.html (1 sheet).

Final Office Action mailed Apr. 16, 2009 from related U.S. Appl. No. 11/609,772.

Office Action mailed Sep. 29, 2008 from related U.S. Appl. No. 11/609,772.

Final Office Action mailed Mar. 18, 2009 from related U.S. Appl. No. 11/537,368.

Office Action mailed Sep. 26, 2008 from related U.S. Appl. No. 11/537,368.

Office Action mailed Dec. 26, 2008 from related U.S. Appl. No. 11/678,565.

Office Action mailed Jan. 25, 2006 from related United States Patent No. 7,125,397.

Notice of Allowance mailed Jun. 28, 2006 from related United States Patent No. 7,125,397.

Corrected Notice of Allowability mailed Oct. 4, 2006 from related United States Patent No. 7,125,397.

Response to 312 Amendment mailed Jan. 3, 2007 from related United States Patent No. 7,214,211.

Notice of Allowance mailed Sep. 19, 2006 from related United States Patent No. 7,214,211.

Advisor Action mailed May 5, 2006 from related United States Patent No. 7,214,211.

Final Office Action mailed Apr. 4, 2006 from related United States Patent No. 7,214,211.

Office Action mailed Jul. 28, 2005 from related United States Patent No. 7,214,211.

Office Action mailed May 18, 2005 from related United States Patent No. 7,214,211.

Office Action mailed Nov. 16, 2006 from related United States Patent No. 7,214,211.

Office Action mailed Jan. 3, 2007 from related United States Patent No. 7,214,211.

Office Action mailed Dec. 5, 2008 from related U.S. Appl. No. 11/326,780.

Office Action mailed Oct. 23, 2007 from related U.S. Appl. No. 10/734,931.

Final Office Action mailed Apr. 8, 2008 from related U.S. Appl. No. 10/734,931.

Examiner's Answer mailed Dec. 30, 2008 from related U.S. Appl. No. 10/734,931.

Office Action mailed Aug. 13, 2004 from related United States Patent No. 7,264,61.

Office Action mailed Dec. 1, 2004 from related United States Patent No. 7,264,613.

Final Office Action mailed May 13, 2005 from related United States Patent No. 7,264,613.
Office Action mailed Feb. 10, 2006 from related United States Patent No. 7,264,613.
Final Office Action mailed Nov. 17, 2006 from related United States Patent No. 7,264,613.
Advisory Action mailed Dec. 27, 2006 from related United States Patent No. 7,264,613.
Notice of Allowance mailed Feb. 7, 2007 from related United States Patent No. 7,264,613.
Office Action mailed Sep. 18, 2002 from related United States Patent No. 6,616,630.
Office Action mailed Dec. 31, 2002 from related United States Patent No. 6,616,630.
Notice of Allowance mailed Apr. 28, 2003 from related United States Patent No. 6,616,630.
Office Action mailed Sep. 10, 1999 from related United States Patent No. 6,287,278.
Office Action mailed Nov. 22, 1999 from related United States Patent No. 6,287,278.
Final Office Action mailed Dec. 11, 2000 from related United States Patent No. 6,287,278.
Final Office Action mailed Feb. 14, 2001 from related United States Patent No. 6,287,278.
Notice of Allowance mailed Jun. 14, 2001 from related United States Patent No. 6,287,278.
Office Action mailed Apr. 22, 1999 from related United States Patent No. 6,117,108.
Final Office Action mailed Sep. 14, 1999 from related United States Patent No. 6,117,108.
Notice of Allowance mailed Feb. 8, 2000 from related United States Patent No. 6,117,108.
Office Action mailed Apr. 30, 1998 from related U.S. Appl. No. 08/915,148.
Office Action mailed Jul. 20, 1998 from related U.S. Appl. No. 08/915,148.
Office Action dated Jul. 28, 2005 from U.S. Appl. No. 10/455,166, filed May 23, 2003.
Related to U.S. Appl. No. 11/326,780, filed Jan. 5, 2006, which is a continuation of U.S. Appl. No. 10/734,931, filed Dec. 12, 2003, which is a CIP of U.S. Appl. No. 10/445,166.
Complaint for Case No. 09 CV 00347, filed May 13, 2009, District of Delaware, United States District Court (40 pages).
B. Braun Melsungen AG's Response to Opposition of Communication dated Sep. 26, 2005 and two (2) Notices of Opposition of Termuno: Response to Opposition dated Mar. 24, 2006, filed by Klingseisen of Zumstein & Klingseisen. including supporting documents (39 pages).
Australian Patent No. 783650, Published Feb. 21, 2002, Applicant's B. Braun Melsungen AG, entitled "Intravenous Catheter Device" 23 (pages).
Statutory Declaration of Joseph J. Chang, Executed and Notarized on Jan. 9, 2007, In the matter of Australian Patent Acceptance No. 783650 and in the Matter of Opposition thereto by Smiths Medical ASD, Inc. (16 pages).
Australian Statement of Grounds and Particulars of Opposition from Medex, Inc., Spruson & Ferguson dated May 17, 2006 regarding Patent Application No. 783650 (2 pages).
Notice of Opposition to a European Patent; Opponents Smiths Medical ASD Inc.; to B. Braun Melsungen AG for Opposed Patent No. 1 180 381; Application No. 01 109 231.9; dated Sep. 27, 2006 (25 pages).
Notice of Opposition to a European Patent; Opponent Terumo Corporation; to B. Braun Melsungen AG for Opposed Patent No. EP 1 003 588 B1; Application No. 98 948 843.2; dated Aug. 16, 2005 (17 pages).
Notice of Opposition to a European Patent; Opponent Medex, Inc.; to B. Braun Melsungen AG for Opposed Patent No. 1 003 588; Application No. 98 948843.2; dated Aug. 17, 2005 (26 pages).
Affidavit of Joseph J. Chang; In the Court of the Commissioner of Patents for the Republic of South Africa; Case No. Patent 2001/3937; In the matter between: B. Braun Melsungen AG (First Applicant), B. Braun Medical (Proprietary) Limited (Second Applicant) and Specialised Systems Electro Medical (Proprietary) Limited (Respondent dated May 6, 2004 (84 pages).
Supplementary Answering Affidavit of Dennis Bialecki; In the Court of the Commissioner of Patents for the Republic of South Africa; Case No. Patent 2001/3937; In the matter between: B. Braun Melsungen AG (First Applicant), B. Braun Medical (Proprietary) Limited (Second Applicant) and Specialised Systems Electro Medical (Proprietary) Limited (Respondent) dated Sep. 15, 2005 (35 pages).
Replying Affidavit of Kevin Woehr; In the Court of the Commissioner of Patents for the Republic of South Africa; Case No. Patent 2001/3937; In the matter between: B. Braun Melsungen AG (First Applicant), B. Braun Medical (Proprietary) Limited (Second Applicant) and Specialised Systems Electro Medical (Proprietary) Limited (First Respondent) dated Oct. 19, 2005 (34 pages).
Affidavit of Kevin VVoehr; In the Court of the Commissioner of Patents for the Republic of South Africa; Case No. Patent 2001/3937; In the matter between: B. Braun Melsungen AG (First Applicant), B. Braun Medical (Proprietary) Limited (Second Applicant) and Specialised Systems Electro Medical (Proprietary) Limited (First Respondent) and The Registrar of Patents (Second Respondent) dated Jun. 4, 2004 (16 pages).
Amended Sheet of Claims for South African Serial No. 2001/3937; filed Oct. 22, 2003; Claims 1-12 (8 sheets) and Figures 1-10 (3 sheets) (11 sheets total).
Affidavit of Dennis Bialecki; In the Court of the Commissioner of Patents for the Republic of South Africa; Case No. Patent 2001/3937; In the matter between: B. Braun Melsungen AG (First Applicant), B. Braun Medical (Proprietary) Limited (Second Applicant) and Specialised Systems Electro Medical (Proprietary) Limited (First Respondent), The Registrar of Patents (Second Respondent) and Medex Inc. (Third Respondent) dated Oct. 13, 2004 (33 pages).
Affidavit of Kevin Woehr; In the Court of the Commissioner of Patents for the Republic of South Africa; Case No. Patent 2001/3937; In the matter between: B. Braun Melsungen AG (First Applicant), B. Braun Medical (Proprietary) Limited (Second Applicant) and Specialised Systems Electro Medical (Proprietary) Limited (First Respondent), The Registrar of Patents (Second Respondent) and Medex Inc. (Third Ressondent) dated Nov. 22, 2004 (38 pages).
In the Court of the Commissioner of Paten for the Republic of South Africa, entitled "Supplemental Answering Affidavit," Case No. Patent 2001/3937. B. Braun Melsungen AG (First Applicant) and B. Braun Medical (Proprietary) Limited (Second Applicant) and Specialised Systems Electro Medical (Proprietary) Limited (Respondent), in regards patent of addition 2001/3937 and an application for infringement thereof, Affidavit of Dennis Bialecki, dated an signed Sep. 1, 2005 (36 pages).
Letter to Commissioner, dated Aug. 18, 2006, U.S. Appl. No. 10/445,166, filed May 23, 2003, entitled "Spring Clip Safety IV Catheter," Confirmation No. 1659, executed by Tom H. Dao, Registration No. 44,641 (3 pages).
Administrative Declaration of Nullity requested by a Counterclaim against Patent No. 218,845, entitled "Spring Clip as Needle Tip Protection for an IV Safety Catheter," *B. Braun Melsungen AG* vs. *Medex De Mexico, S.A. De C.V*, (58 pages).
Mexican Institute of Industrial Property Division Direction for the Protection of Intellectual Property Divisional Subdirection of Industrial Property Processes Department Coordination of Cancellation and Lapsing, N-2 Response to the Petition for the Administrative Declaration of Nullity of Patent 218,845, entitled "Spring Clip as Needle Tip Protection for an IV Safety Catheter," Case No, P.C. 664/2004 (n-358) 9767 (33 pages).
Nullity of the Patent of invention PI9812128-6, filed on Aug. 18, 1998 and issued on Mar. 30, 2004, in the name of B. Braun Melsungen AG under the Title "IV Catheter and Catheter Device," Signed by Antonio M.P. Arnaud, Sao Paulo, Sep. 29, 2004 (21 pages).
Response to the Request of Administration Nullity of the Patent PI9812128-6, dated Mar. 30, 2004, Patentee: B. Braun Melsungen AG, entitled "Catheter and Catheter Device," Rio de Janeiro, Feb. 28, 2005, Momsen, Leonardos& CIA (8 pages).
Technical Report Published on Jul. 26, 2005. Brazilian Patent No. PI9812128-6, PCT/EP98/05231, filed Aug. 18, 1998, Applicant: B. Braun Melsungen AG, Granting Date: Mar. 30, 2004, entitled "IV Catheter and Catheter Device," dated Jun. 29, 2005, signed by Vania Gouvea Geraidina, Andriana Briggs de Aguiar, Patent Examiners, in agreement, signed by Leila Freire Falcone, Coordinator of the Appeal and Administrative Nullity Section (4 pages).

Response to the Technical Report Regarding the Request for Administrative Nullity of the Patent PI0812128-6, dated Mar. 30, 2004, Patentee: B. Braun Melsungen AG, entitled "IV Catheter and Catheter Device," Rio de Janeiro, Sep. 26, 2005, Momsen, Leonardos & CIA (9 pages).

Lawsuit: Your Honor the Federal Judge of the Federal Court of the Rio de Janeiro District Court, *B. Braun Melsungen AG* vs. *National Institute of Industrial Property—INPI* (1st Defendant) and *Johnson & Johnson Produtos Profissionais LTDA* (2nd Defendant) (23 pages).

Description of Claims 27 and 28 in regards to Claim 27 vs. US Patent No. 5,5,504, Claim 27 vs. EP554841 and the novelty of PI9812128-6 over US Patent No. 6,652,486, INPI comments regarding the Federal Court action in Brazil (4 pages).

Amended Passages in the Specification, Claims as presented on Jan. 19, 2003, showing the pending claims at issue in the Brazilian nullity action (5 pages).

Information Disclosure Statement (IDS) of Reissue Application Patent No. 6,652,486 B2, Issued Nov. 25, 2006, including Substitute Form PTO-1449. This IDS was cited for U.S. Appl. No. 11/013,289 (6 pages).

Japanese Publication No. P2002-85558A, Publication Date: Mar. 26, 2002, Filing Date: Sep. 19, 2000, includin English Translation.

Prior art drawings of B. Braun Medical Inc., listed as "Ga. Spring Clip Detail for Introcan Catheter", dated Apr. 20, 1999, ref. No. PRE-670, on sale as early as Mar. 2000 (3 sheets).

Prior art drawing by B. Braun Medical, Inc., listed as "Ga. Spring Clip Detail for Introcan Catheter", dated Jun. 15. 1999, ref. No. PRE-671, on sale as early as Mar. 2000 (1 sheet).

Stipulated Protective Order for Case No. 09 CV 00347-JJF-LPS, Document 67, filed Dec. 7, 2009, District of Delaware, United States District Court (17 pages).

Declaration of Michael A. Pearson, Jr. in Support of Braun's Response to Terumo's Counter-Statement in Response to Braun's Motion for Partial Summary Judgment on Terumo's Anticipation and Obviousness Invalidity Defenses and Counterclaims for Certain Claims of the '613 Patent, including Appendixes 15-22; Case No. 09 CV 00347-JJF-LPS, Document 252, filed Aug. 17, 2010; District of Delaware, United States District Court; Redacted—Public Version (82 pages).

Braun's Response to Terumo's Counter-Statements in Response to Braun's Motion for Partial Summary Judgment on Terumo's Anticipation and Obviousness Invalidity Defenses and Counterclaims for Certain Claims of the '613 Patent; Case No. 09 CV 00347-JJF-LPS, Document 251, filed Aug. 17, 2010, District of Delaware, United States District Court; Redacted—Public Version (15 pages).

Declaration of Douglas E. McCann in Support of Terumo's Counter-Statements of Genuine Issues of Material Fact in Response to Braun's Motions for Summary Judgment; Case No. 09 CV 00347-JJF-LPS, Document 234, filed Jul. 29, 2010. District of Delaware, United States District Court; Redacted (22 pages).

Declaration of Dr. John C. Kulli in Support of Terumo's Counter-Statements of Genuine Issues of Material Fact in Response to Braun's Motions for Summary Judgment: Case No. 09 CV 00347-JJF-LPS, Document 233, filed Jul. 29, 2010, District of Delaware, United States District Court: Redacted (75 pages).

Terumo's Counter-Statement of Genuine Issues of Material Fact in Response to Braun's Motion for Partial Summary Judgment on Terumo's Anticipation and Obviousness Invalidity Defenses and Counterclaims for Certain Claims of the '613 Patent; Case No. 09 CV 00347-JJF-LPS, Document 232, filed Jul. 29, 2010, District of Delaware, United States District Court; Redacted (24 pages).

Declaration of Michael A. Pearson, Jr. in Support of Braun's Motion for Partial Summary Judgment on Terumo's Anticipation and Obviousness Invalidity Defenses and Counterclaims for Certain Claims of the '613 Patent; Case No. 09 CV 00347-JJF-LPS, dated Jun. 25, 2010, District of Delaware, United States District Court; Redacted—Public Version (161 pages).

Braun's Opening Brief in Support of its Motion for Partial Summary Judgment on Terumo's Anticipation and Obviousness Invalidity Defenses and Counterclaims for Certain Claims of the '613 Patent; Case No. 09 347 JJF-LPS, dated Jun. 25, 2010, redacted version Jul. 2, 2010, District of Delaware, United States District Court; Redacted—Public Version (22 pages).

Braun's Motion for Partial Summary Judgment on Terumo's Anticipation and Obviousness Invalidity Defenses and Counterclaims for Certain Claims of the '613 Patent; Case No. 09 CV 00347-JJF-LPS, Document 200, filed Jun. 25. 2010, District of Delaware, United States District Court (2 pages).

Opening Expert Report of Dr. John C. Kulli Regarding Certain Claims of U.S. Patent No. 7,264,613, including Appendixes A-J; *B. Braun Melsungen AG & B. Braun Medical Inc.* v. *Terumo Medical Corporation & Terumo Corporation*, dated Apr. 9, 2010 (874 pages).

Terumo Medical Corporation & Terumo Corporation's First Supplemental Responses to B. Braun Melsungen AG & B. Braun Medical Inc.'s First Set of Interrogatories (No. 3), with Attachment a and Appendixes 2-11; Case No. 09-347-JJF, dated Sep. 22, 2009, District of Delaware, United States District Court (1506 pages).

Terumo Medical Corporation & Terumo Corporation's Supplemental Answers to B. Braun Melsungen AG & B. Braun Medical Inc,'s First Set of Interrogatories (nos. 1-6); Case No. 09 347 JJF, dated Dec. 30, 2009, District of Delaware, United States District Court; Redacted (36 pages).

Terumo Medical Corporation & Terumo Corporation's Third Supplemental Answers to B. Braun Melsungen AG & B. Braun Medical Inc.'s First Set of Interrogatories (Nos. 2 and 3); Case No. 09-347-JJF, dated Feb. 26, 2010, District of Delaware, United States District Court; Redacted (23 pages).

Terumo Medical Corporation & Terumo Corporation's Fourth Supplemental Answers to B. Braun Melsungen AG & B. Braun Medical Inc.'s First Set of Interrogatories (No. 3). Case No. 09 347 JJF-LPS, dated Mar. 11, 2010, District of Delaware, United States District Court; Redacted (22 pages).

\* cited by examiner

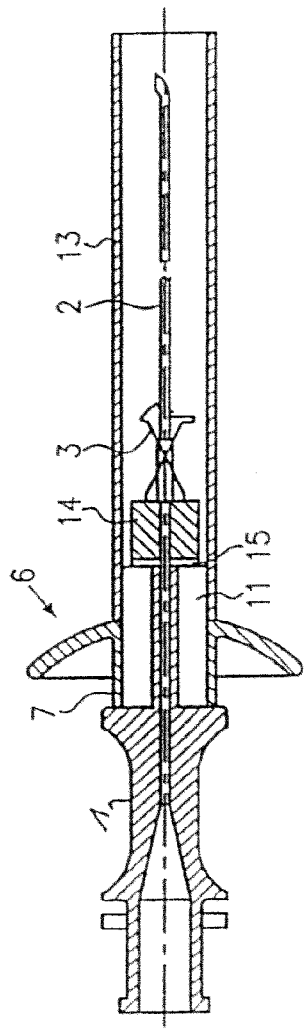
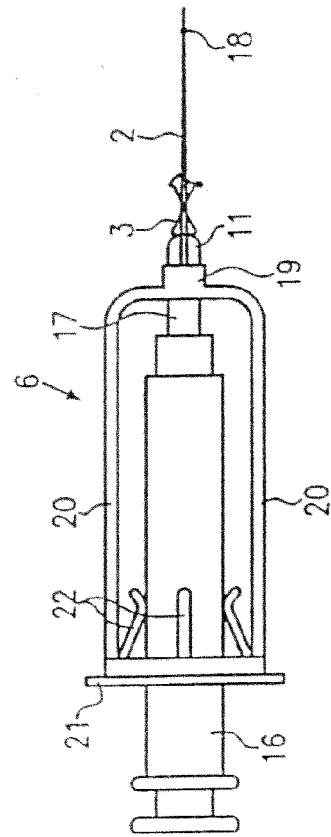
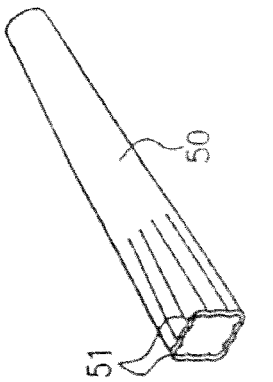
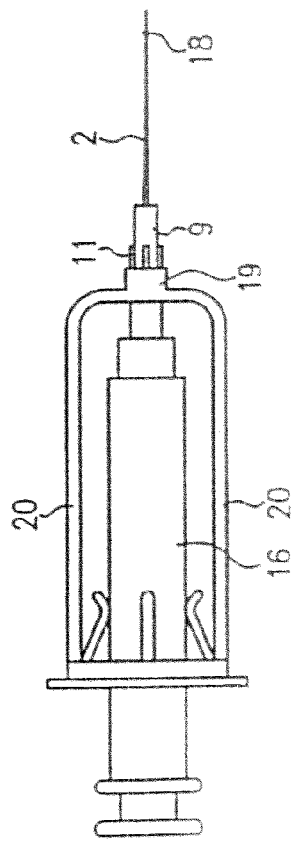
Fig.4
Fig.5
Fig.6
Fig.6a

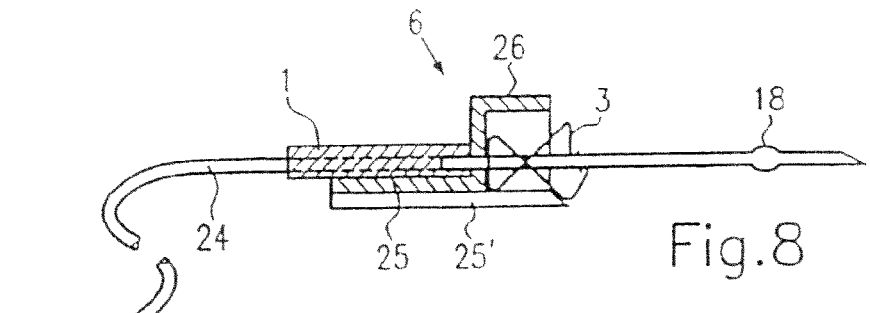
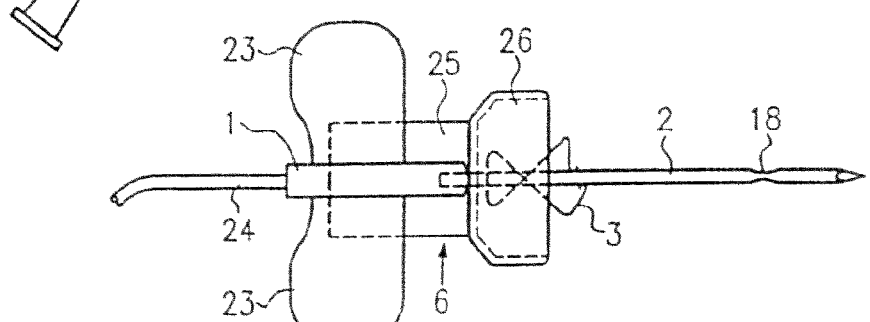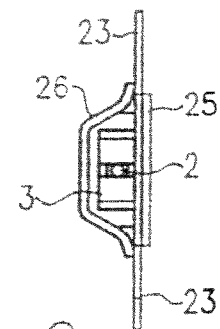
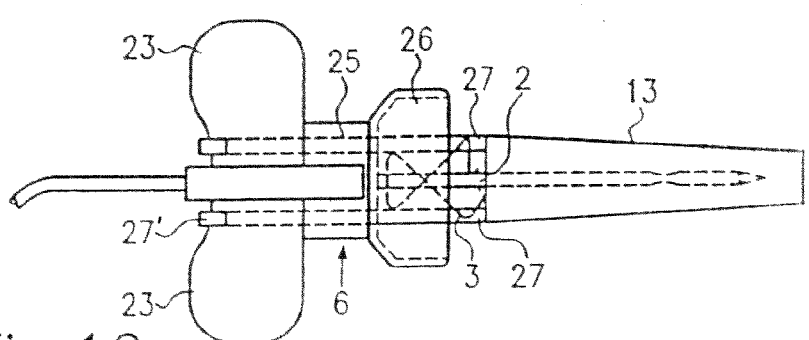
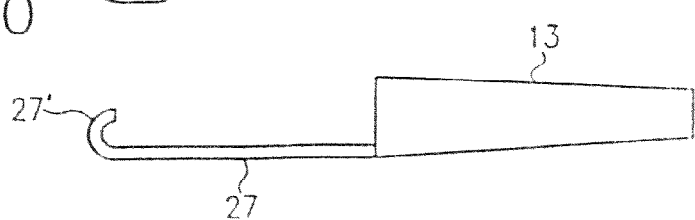

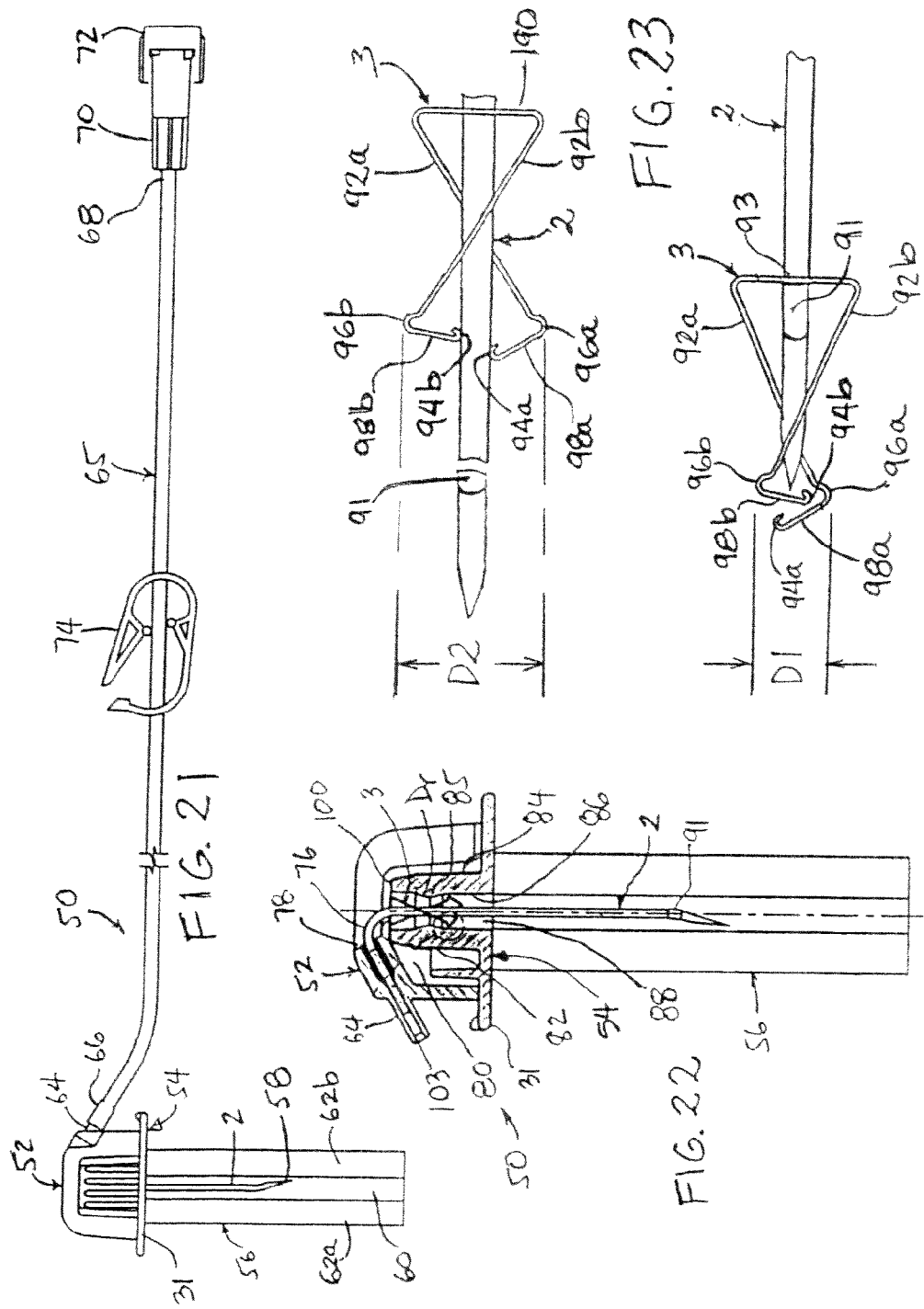

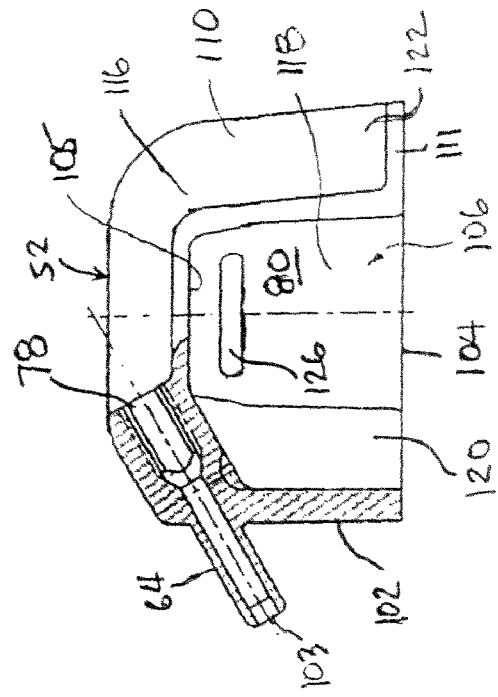

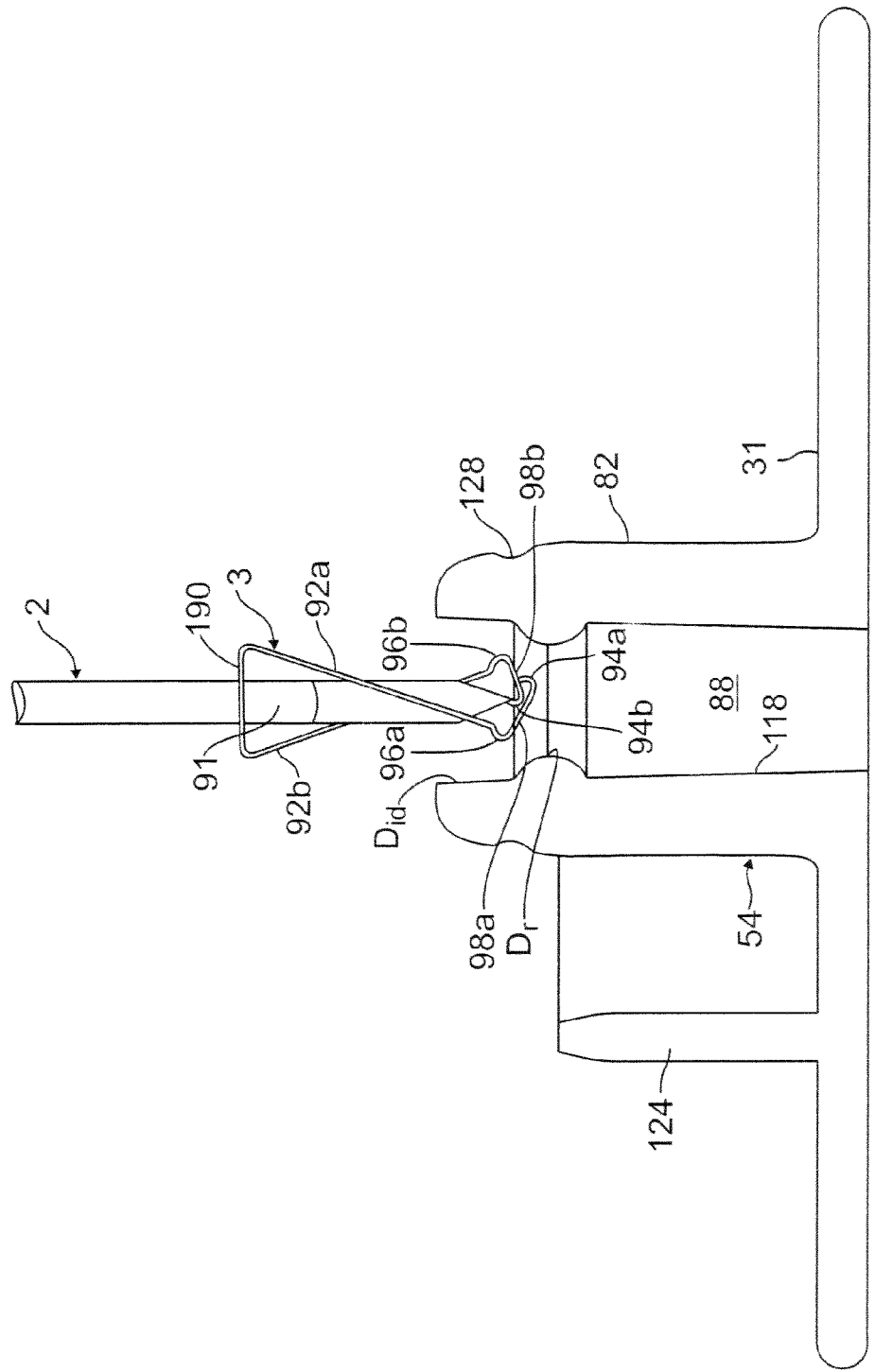

PROTECTIVE DEVICE FOR AN INJECTION NEEDLE

CROSS-REFERENCE TO RELATED APPLICATIONS

This application is a continuation of application of Ser. No. 12/574,963, filed Oct. 7, 2009, now U.S. Pat. No. 8,100,858 which is a continuation of Ser. No. 11/537,368; filed Sep. 29, 2006, now U.S. Pat. No. 7,611,487, which is a divisional application of Ser. No. 10/856,315, filed May 27, 2004, now U.S. Pat. No. 7,125,397, which is a continuation-in-part of an application entitled PROTECTIVE DEVICE FOR AN INJECTION NEEDLE, application No, 10/468,923, filed Feb. 2, 2004, now U.S. Pat. No. 7,214,211, which claims priority to international application No. PCT/EP02/02042, entitled PROTECTIVE DEVICE FOR AN INJECTION NEEDLE, filed Feb. 26, 2002, which claims the benefit of German application No. 201 03 363, filed Feb. 26, 2001, the contents of which are expressly incorporated herein by reference.

BACKGROUND

Protective devices for covering needle tips are well known, for example from U.S. Pat. No. 4,929,241, wherein a relatively small protective element is arranged on a needle and can be moved by a spring from a retracted or ready position to a protected position on the needle tip. The elastic arms of the protective element engage over the needle tip while an engagement device on the protective element holds the latter on the needle shaft. Because of the relatively small size of the protective element, it is difficult to move it by hand on the needle. In addition, the securing spring can only be released when the needle tip lies free so that a risk of injury cannot be ruled out.

Accordingly, there is a need for a needle assembly that has an easy to use grip part for moving the protective element, which is positioned between the protective element and the needle holder or hub.

SUMMARY

The present invention may be implemented by providing a needle assembly comprising a needle holder comprising a body comprising a channel extending at least a portion of the body, an interior cavity in communication with the channel; a needle holding sleeve, and a Huber needle comprising a needle shaft attached to the needle holding sleeve; said Huber needle comprising a bent section along a portion of the needle shaft; a middle retaining portion removably received in the interior cavity of the needle holder, the middle retaining portion comprising a flange, a tubular projection, and a bore extending through the tubular projection and the flange having the Huber needle extending through the bore; said bore comprising a first section comprising a first dimension and a second section comprising a second dimension; and a protective element coaxially disposed with the needle shaft and positioned inside the bore; said protective element comprising a distal portion comprising a third dimension when positioned inside the bore and a fourth dimension when separated from the bore. In one exemplary embodiment, the first dimension is larger than the third dimension, which is larger than the second dimension, which is larger than the fourth dimension.

In another aspect of the present invention, there is provided a needle assembly comprising a needle holder comprising a body comprising a channel extending at least a portion of the body, an interior cavity in communication with the channel, a needle holding sleeve, and a Huber needle comprising a needle shaft attached to the needle holding sleeve; said Huber needle comprising a bent section along a portion of the needle shaft and a needle tip; a middle retaining portion removably received in the interior cavity of the needle holder comprising a flange, a tubular projection, a bore extending through the tubular projection and the flange, and the Huber needle extending through the bore; said bore comprising a wall surface comprising a wall engagement structure; and a protective element coaxially disposed with the needle shaft and positioned inside the bore; said protective element engaging the wall engagement structure of the bore when the Huber needle is moved relative to the middle retaining portion. In one exemplary embodiment, the protective element is disengaged from the wall engagement structure of the bore when the needle tip moves from a position distal of a finger portion of the protective element to a position proximal of the finger portion of the protective element.

In yet another aspect of the present invention, there is provided a needle assembly comprising a needle hub comprising a base section, a nose section, an exterior surface, and a interior surface defining an interior cavity; a needle comprising a needle shaft, a distal end comprising a needle tip, and a proximal end attached to the nose section of the needle hub; a middle retaining portion telescopically disposed over at least a portion of the nose section of the needle hub comprising a body structure comprising an exterior surface and an interior surface defining a bore; said bore comprising a wall surface comprising a wall engagement structure; and a protective element coaxially disposed with the needle shaft and positioned at least partially inside the bore of the middle retaining portion; said protective element engaging the wall engagement structure of the bore when the needle is moved relative to the middle retaining portion. In one exemplary embodiment, the protective element is disengaged from the wall engagement structure of the bore when the needle tip moves from a position distal of a finger portion of the protective element to a position proximal of the finger portion of the protective element.

In still yet another aspect of the present invention, there is provided a needle assembly comprising a needle hub comprising a base section, a nose section, an exterior surface, and a interior surface defining an interior cavity; a needle comprising a needle shaft, a distal end comprising a needle tip, and a proximal end attached to the nose section of the needle hub; a middle retaining portion telescopically disposed over at least a portion of the nose section of the needle hub comprising a body structure comprising an exterior surface and an interior surface defining a bore; said bore comprising a first section comprising a first dimension and a second section comprising a second dimension; and a protective element coaxially disposed with the needle shaft and positioned at least partially inside the bore of the middle retaining portion; said protective element comprising a distal portion comprising a third dimension when positioned inside the bore and a fourth dimension when separated from the bore. In one exemplary embodiment, the first dimension is larger than the third dimension, which is larger than the second dimension, which is larger than the fourth dimension.

BRIEF DESCRIPTION OF THE DRAWINGS

These and other features and advantages of the present invention will become appreciated as the same become better understood with reference to the specification, claims and appended drawings wherein:

FIG. 4 shows a modified device according to FIGS. 1 and 2 with a needle cap;

FIG. 5 shows another embodiment of a grip part in conjunction with a syringe;

FIG. 6 shows a modified embodiment of the device according to FIG. 5;

FIG. 7 shows an embodiment in conjunction with a needle holder provided with wings;

FIG. 8 shows a cross section through the embodiment according FIG. 7;

FIG. 9 shows an end view of FIG. 7;

FIG. 10 shows a plan view of an embodiment according to FIG. 7 with needle cap;

FIG. 11 shows a view of the needle cap according to FIG. 10;

FIG. 21 is a semi-schematic side view of another alternative needle assembly provided in accordance with aspects of the present invention;

FIG. 22 is a semi-schematic cross-sectional side view of the needle assembly of FIG. 21 from a different angle without the tubing;

FIG. 23 is a semi-schematic exemplary partial side view of the needle and the protective element of FIG. 21 shown separated from the needle holder and middle retaining portion for clarity;

FIG. 24 is a semi-schematic perspective view of the needle holder of FIG. 21 without the needle or the hose for clarity;

FIG. 25 is a semi-schematic cross-sectional side view of the needle holder of FIG. 24;

FIG. 26 is a semi-schematic bottom view of the needle holder of FIG. 24;

FIG. 27 is a semi-schematic cross-sectional side view of the middle retaining portion of FIG. 22;

FIG. 28 is a semi-schematic partial cross-sectional side view of the protective element activated over the needle and separated form the middle retaining portion;

DETAILED DESCRIPTION OF THE INVENTION

The detailed description set forth below in connection with the appended drawings is intended as a description of the presently preferred embodiments of protective devices for injection needles provided in accordance with practice of the present invention and is not intended to represent the only forms in which the present invention may be constructed or utilized. The description sets forth the features and the steps for constructing and using the protective devices of the present invention in connection with the illustrated embodiments. It is to be understood, however, that the same or equivalent functions and structures may be accomplished by different embodiments that are also intended to be encompassed within the spirit and scope of the invention. Also, as denoted elsewhere herein, like element numbers are intended to indicate like or similar elements or features.

Figure 1:
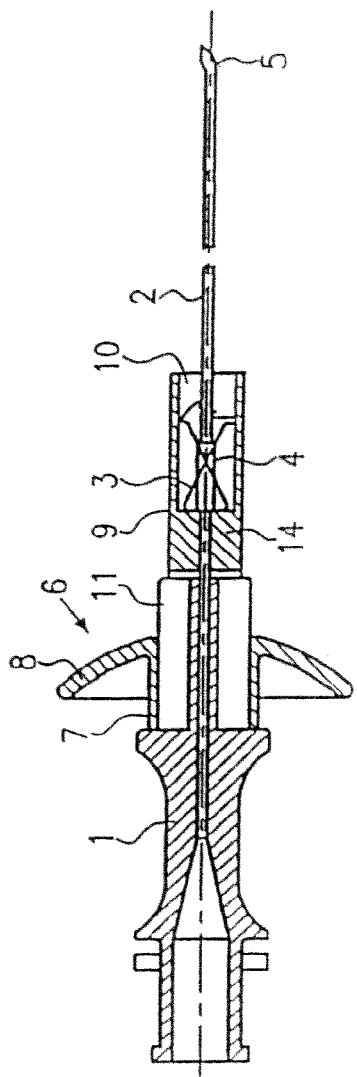
FIG. 1 shows a protective device in longitudinal section.

FIG. 1 shows a needle holder 1 in which a needle 2 is secured. Arranged on the shaft of the needle 2 there is a protective element 3 in the form of a spring clip with intersecting arms. Reference number 4 indicates a sleeve which can be moved with the protective element 3 along the needle shaft. In the illustrative embodiment shown, the tip 5 of the needle is designed with a curve in the manner of an epidural needle or a Huber needle, so that the sleeve 4, which has a smaller diameter than the curve on the needle tip, and, together with it, the protective element 3 and cannot be moved past the needle tip.

Arranged between needle holder 1 and protective element 3 there is a grip part 6 which, at the proximal end, has a hollow cylindrical portion 7 on which a radially protruding shield 8 is formed. On the front face of the shield 8 there is a cylindrical portion 9 whose distal end is hollow. In the standby position according to FIG. 1, the protective element 3 is arranged in the cavity 10 and, by displacement of the grip part 6, can be moved forward to the needle tip 5, while the needle holder 1 is held with the other hand. The angled ends of the intersecting arms of the protective element 3 engage over the needle tip 5, so that injury to operating personnel by the needle tip is prevented.

Figure 2:
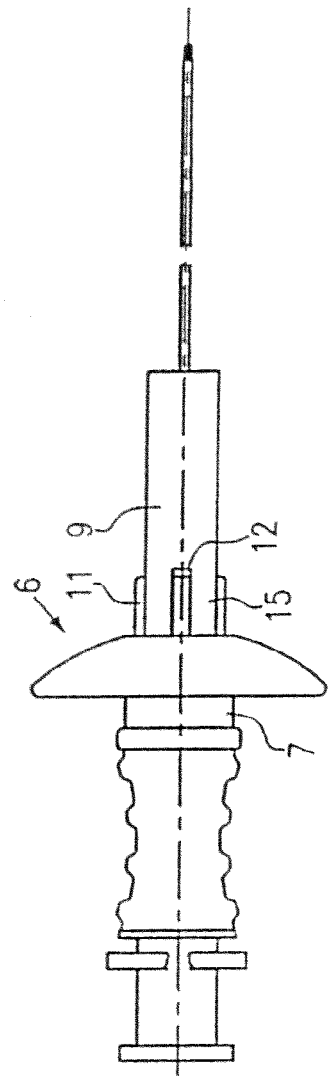
FIG. 2 shows a side view of the embodiment according to FIG. 1.

At the distal end, the needle holder 1 has radially protruding ribs 11 on which the hollow cylindrical portion 7 of the grip part 6 is guided. Between the cylindrical portion 9 of smaller external diameter and the hollow cylindrical portion 7 of greater external diameter, slits 12 are formed in the grip part 6, through which slits 12 the front ends of the ribs 11 of the needle holder 1 protrude radially, as FIG. 2 shows.

The cylindrical portion 9 of the grip part 6 provided with the cavity 10 has a solid cylindrical portion 14 between the slits 12 and the cavity 10, in the central bore of which portion 14 the needle 2 is guided. Between the slits 12 of the grip part 6, the cylindrical portion 9 is connected integrally to the shield 8 and the hollow cylindrical portion 7 via bridges 15.

These ribs 11 protruding over the outer circumference of the cylindrical portion 9 of the grip part 6 serve for attachment of a needle cap 13, which is shown in FIG. 4. This needle cap 13 is used for storing and handling the device. It can be removed from the needle holder 1 immediately before use of the injection needle, in order to expose the needle, without the grip part 6 and the protective element 3 being moved, because the needle cap 13 is held by the ribs 11 at a radial distance from the portion 9 of the grip part 6.

Because of the smaller diameter at the portion 14 compared to the greater diameter at the ribs 11, the needle cap 13, which consists of a tube section of constant diameter, cannot be positioned incorrectly on the portion 14, but only attached to the ribs 11. This ensures that the needle cap 13 is not inadvertently engaged with a portion of the grip part 6. The needle cap 13 can be produced inexpensively by extrusion of a tube, a section of such a tube forming the needle cap 13.

After removal of the needle cap 13, an injection can be carried out in the standby position according to FIGS. 1 and 2. As the needle is pulled back with one hand on the needle holder 1, the grip part 6 on the portion 7 is held with the other hand, so that the protective element 3 is moved into the protection position on the needle tip as a result of the relative movement between grip part 6 and needle 2. This deployed position of the grip part 6 is illustrated in FIG. 3.

Figure 3:
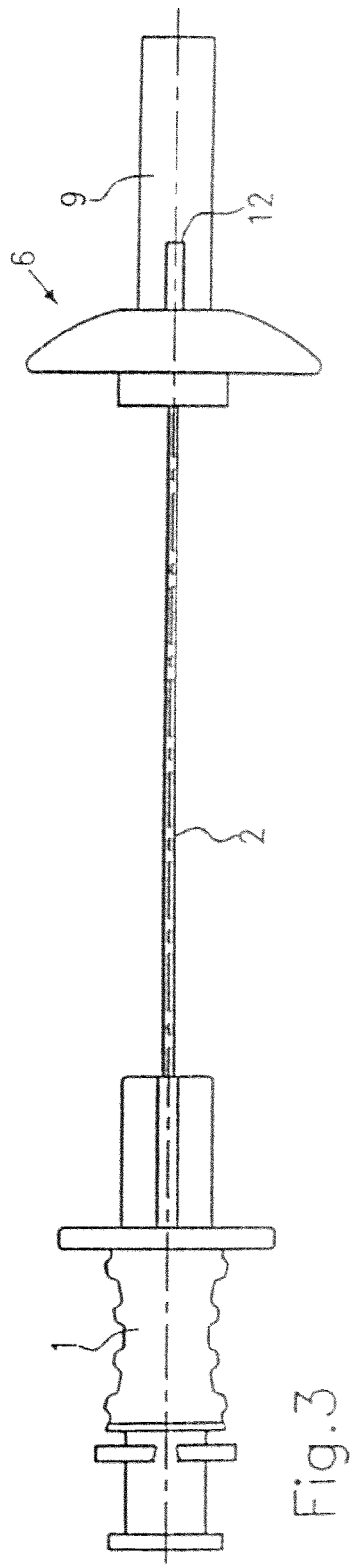
FIG. 3 shows a view of the device according to FIGS. 1 and 2 with the protective element moved to the protection position.

The protective element 3 is arranged loosely in the cavity 10 of the grip part 6, so that the rip part 6 can be easily drawn back from the position in FIG. 3, while the protective element remains in the protection position on the needle tip. The cavity 10 in the cylindrical portion 9 protects the protective element 3 after removal of the needle cap 13.

FIG. 4 shows a preferred embodiment of the grip part 6, the hollow cylindrical portion at the distal end of the grip part 6 being omitted, so that the solid cylindrical portion 14 forms the distal end of the grip part 6. After removal of needle cap 13 from the ribs 11, the protective element 3 lies free in FIG. 4.

In the embodiment according to FIGS. 1 and 2, the hollow cylindrical portion 7 on the grip part 6 is used to protect the fingers of the hand holding the grip part from touching the needle shaft when the needle is drawn back.

In another configuration of the needle holder 1, this hollow cylindrical portion 7 can be made larger behind the shield 8.

The grip part 6, like the needle holder 1 too, is expediently made of plastic.

FIG. 5 shows a modified embodiment of a grip part 6 in combination with a syringe 16 on which an injection needle 2 is secured via a needle holder 17 designed as cannula attachment. In this embodiment, a bead 18 is formed on the outer circumference of the needle, before the needle tip, on which bead 18 the rear wall of the protective element 3 comes to bear in the protection position. Instead of a bead 18, diametrically opposite knob-like projections can be formed by pinching the needle.

The grip part 6 has a cylindrical portion 19 which, in the starting position according to FIG. 5, is guided on the needle holder 17. In the illustrative embodiment shown, two brackets 20 extend from this cylindrical portion 19 in the proximal direction, on diametrically opposite sides, at a distance from the syringe circumference. The ends of these brackets 20 are integrally formed on an annular body 21 from which elastic fingers 22 extend radially inward. The free ends of these elastic fingers 22 lie on the outer circumference of the syringe 16.

Because of the elastic fingers 22 between the grip part 6 and the outer circumference of the syringe 16, the grip part 6 can be used for different sizes of syringe diameter, e.g. syringes with a volume of 1 ml to 10 ml can be fitted into the same grip part. By this means, there is a wide choice of syringes which can be used with the same needle.

In the embodiment according to FIG. 5 too, radially protruding ribs 11 are formed at the front end of the needle holder formed as cannula attachment and these serve as a seat for a needle cap. The protective element 3, whose rear wall protrudes beyond the cross section of the ribs 11, is moved forward into the protection position through the inner circumference of the cylindrical portion 19.

FIG. 6 shows an embodiment of the grip part 6 in which, formed on the cylindrical portion 19, there is a further cylindrical portion 9 in whose cavity 10 the protective element 3 is received. As in the embodiment according to FIGS. 1 and 2, axially extending slits are formed between cylindrical portion 19 and portion 9, through which slits the ribs 11 formed on the needle holder or cannula attachment 17 protrude in order to receive the needle cap 13.

FIG. 6a shows, in a perspective view, a needle cap 50 which is formed by injection-molding and whose distal end can be closed, while the proximal end has, on the inner circumference, flutes or grooves 51 which correspond to the number of ribs 11 and which engage with the ribs 11 when the needle cap is placed on the needle holder 17, so that, by turning the attached needle cap 50, the needle holder 17 can also be turned. A threaded engagement is usually provided between needle holder 17 and syringe 16, so that, by turning the needle cap 50, the needle holder 17 can be screwed onto the syringe 16.

It is customary to draw liquid into the syringe by means of a needle of relatively large diameter and then to replace this needle with a needle having a relatively small diameter, in order to perform an infusion on the patient. In the embodiment according to FIGS. 5 and 6, the needle can be changed without difficulty.

The described design permits actuation with one hand when the syringe content has been injected, the syringe 16 being held with two fingers and the needle being pulled from the patient's skin, while at the same time a finger of the hand bears on the annular body 21 lying at the proximal end.

FIG. 7 shows a plan view of a needle holder 1 which is provided with laterally protruding wings 23 and to which a connection tube 24 is attached. Arranged between the protective element 3 arranged on the needle shaft and the needle holder 1 there is a grip part 6 with a hub-shaped portion 26 which, because of the flat injection angle (FIG. 8), expediently has a surface part 25 for bearing on the patient's skin which, on the bearing side, can be provided for example with an adhesive layer for better retention on the skin. A foam material 25' is preferably provided on the bearing side. The hub portion 26 of the grip part 6 protruding from the front end of the surface part 25 at least partially covers the protective element 3. The surface part 25 or the soft bearing part 25 also serves as spacer for keeping the protective element 3 from the patient's skin. In the illustrative embodiment according to FIG. 8, the soft bearing part 25' extends across the surface part 25 under the huh portion 26, so that the protective element 3 does not lie on the patient's skin.

The needle holder 1 provided with wings 23 is used for venous infusions, for which a thin needle is normally used. The wings 23 are relatively large and flexible. They are pressed together if the needle is introduced into the skin at a very flat angle. A protective paper (not shown) applied on the adhesive layer on the bearing surface should not be peeled off until the needle is introduced into the vein. After the needle has been introduced into the vein, the wings 23 are placed flat against the patient's skin and secured with an adhesive tape. The grip part 6 too can be secured by means of an adhesive tape, the hub-shaped portion 26 preventing contact between protective element 3 and adhesive tape. When the needle is drawn back after removal of the adhesive tape from the needle holder, the grip part 6 initially remains in its position with the protective element 3. After the drawn-back needle tip is safely covered by the protective element 3, with the projections 18 on the needle fixing the protective element 3 on the needle tip, the grip part 6 can also be removed from the patient's skin.

FIGS. 7 and 8 show the device in the standby position for insertion of the needle. If the bearing surface 25 provided with an adhesive layer is used on the grip part, this is a passive system.

FIG. 9 shows a view of the grip part 6 from the right in FIG. 7. The wings 23 serve as bearing surface for the needle holder 1 since the infusion needle must remain for a certain time in the inserted position.

FIGS. 10 and 11 show, in a construction according to FIGS. 7 through 9, a needle cap 13 provided with two spaced-apart retaining brackets 27 which are hooked via a curved free end 27' on the wings 23, as FIG. 10 shows. In this embodiment, the proximal end of the needle cap 13 expediently bears on the front end of the protective element 3, as FIG. 10 shows, so that the protective element 3 is held in its standby position.

It is also possible, however, to provide a hub-shaped attachment at the proximal end of the needle cap 13, which attachment bears on the front face of the hub-shaped portion 26.

In the embodiments described, a protective element in the form of a spring clip with intersecting arms is depicted in each case. However, another design of a protective element can also be used in conjunction with the grip part 6.

Figure 12:
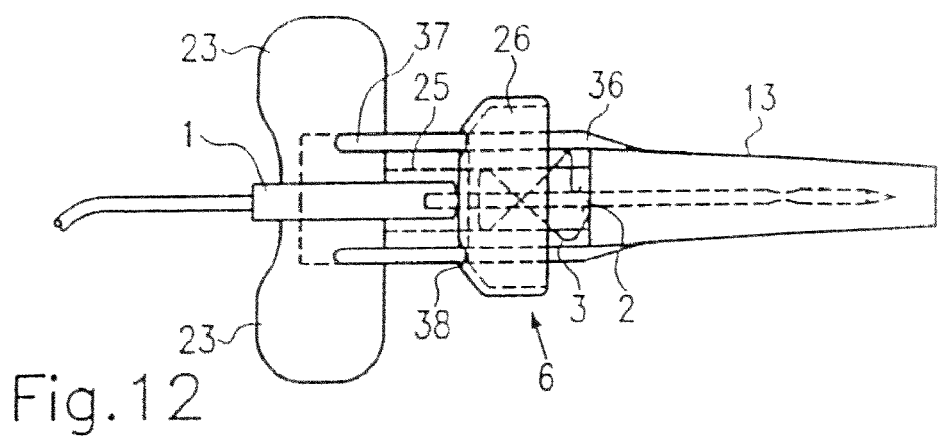
FIG. 12 shows a plan view of an embodiment according to FIG. 7 with a modified needle cap.
Figure 13:
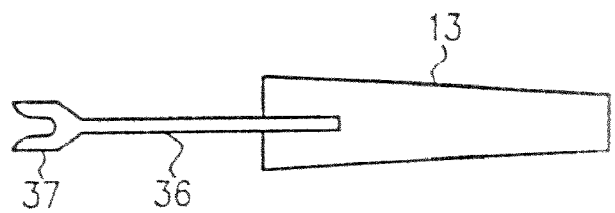
FIG. 13 shows a side view of the needle cap according to FIG. 12.

FIG. 12 shows a further embodiment of the device according to FIGS. 7 through 9. Instead of having the suspension brackets 27, the needle cap 13 is in this case provided on both sides with an extension strut 36 which, at the free end, has a fork-shaped portion 37 for attachment to the wings 23 of the needle holder (FIG. 13). These two spaced-apart struts 36 extend through correspondingly dimensioned openings 38 in the hub portion 26 of the grip part 6, so that the fork-shaped insertion portions 37 can be pulled without difficulty through these openings 38. When the needle cap 13 is taken off, the needle holder 1 is held, and the grip part 6 is not moved.

Figure 14:
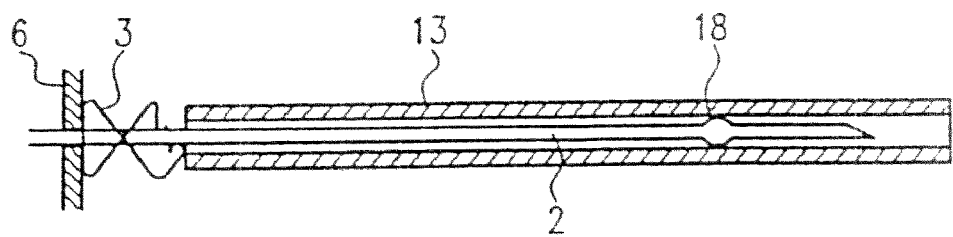
FIG. 14 shows a longitudinal section through a needle cap.

FIG. 14 shows a longitudinal section through a needle cap 13 whose proximal end bears on the protective element 3. The needle cap is of tubular design, and the diameter enlargement 18 on the needle 2, produced by pinching, serves as a spacer for the needle cap 13. Such a needle cap can be produced by extrusion or injection-molding. It is also possible to form, on the inner circumference of the needle cap, a bead or knobs, which bear on the needle shaft and guide the needle substantially concentrically in the needle cap. The needle cap 13 is in this case held on the needle 2 by friction on the bulges 18.

According to a further embodiment, the needle cap, when it has been fitted onto the needle, can be fixed on the needle by mean of heat and pressure or by shrinking.

Figure 15:
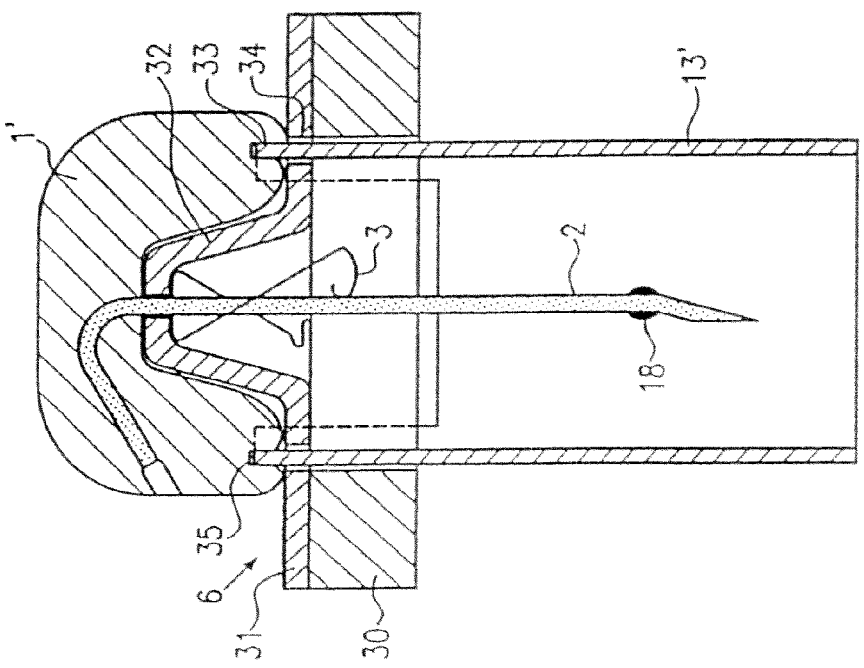
FIG. 15 shows a cross section through another embodiment with a curved needle.

FIG. 15 shows an embodiment in combination with a Huber needle 2 which is held in a needle holder 1' by means of a curved portion and is provided for perpendicular insertion upon injection. Reference number 30 designates a bearing part which is preferably made of foam material and which is provided with an adhesive face for better fixing on the patient's skin. Arranged between the bearing part 30 and the needle holder 1' there is a shield-like grip part 6 which rests on the bearing part via a flange-like area 31 and extends via a pot-shaped middle portion 32 into a corresponding depression in the needle holder 1' The protective element 3 is arranged in this pot-shaped middle part 32.

When the needle is drawn out, the grip part 6 is held on the bearing part 30, while the needle holder 1' is removed. The protective element 3 is moved toward the needle tip until it comes to rest on the needle bulge 18, while at the same time the two intersecting arms of the protective element 3 engage over the needle tip and cover it. The grip part 6 can be removed from the bearing part 30 or together with the latter. Grip part 6 and bearing part 30 can also be connected to one another via an adhesive layer.

The side walls of the pot-shaped middle part 32 are preferably conical so that the grip part 6 cannot itself be removed but instead only pressed.

FIG. 15 shows a needle cap 13' with a tubular portion from whose proximal end there protrude diametrically opposite wall portions 33 which are inserted via partially circular slits 34 in the flange 31 of the grip part 6 into correspondingly partially circular grooves 35 in the needle holder 1'. The curved wall portions 33 are guided loosely through the curved slits 34 in the flange 31 of the grip part 6 and inserted with a press fit into the grooves 35 of the needle holder 1'.

As in the other embodiments of a needle cap 13, the needle cap 13' in FIG. 15 can also be closed at the distal end.

Figure 16:
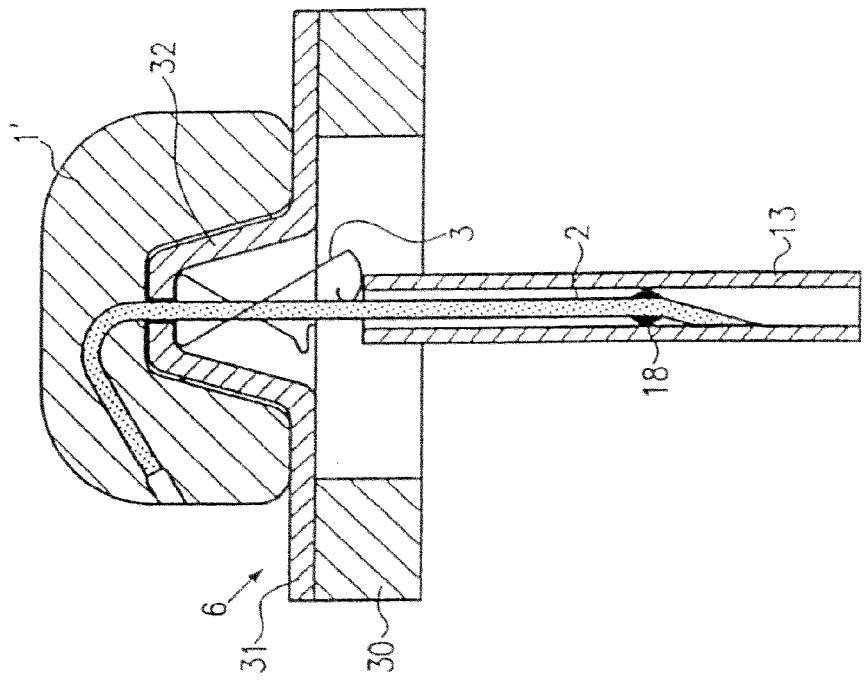
FIG. 16 shows another needle cap in the embodiment according to FIG. 15.
Figure 16A:
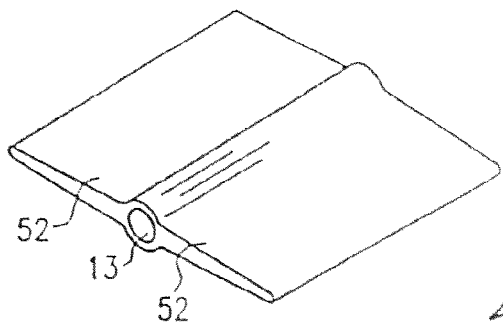

FIG. 16 shows an embodiment with a Huber needle 2 according to FIG. 15, where a needle cap 13 of smaller internal diameter is pushed onto the needle 2. The needle cap corresponds substantially to that of FIG. 14, the needle cap 13 being held on the needle by means of friction at the angled front end. This needle cap 13 in FIG. 16 can be provided with radially protruding and diametrically opposite surface portions 52 through which handling is improved and the tubular needle cap 13 is made more rigid. FIG. 16a shows a perspective view of such a needle cap 13 with diametrically opposite surface portions 52.

Figure 17:
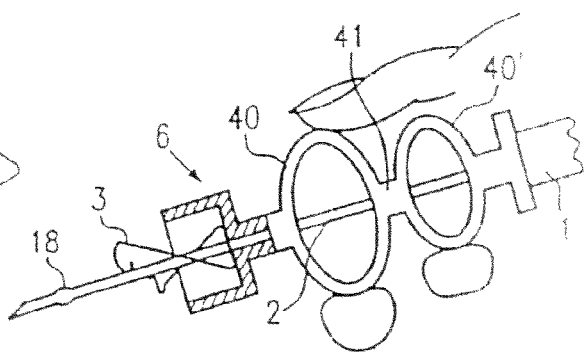
FIG. 17 shows an embodiment with a deformable grip part in the starting position.
Figure 18:
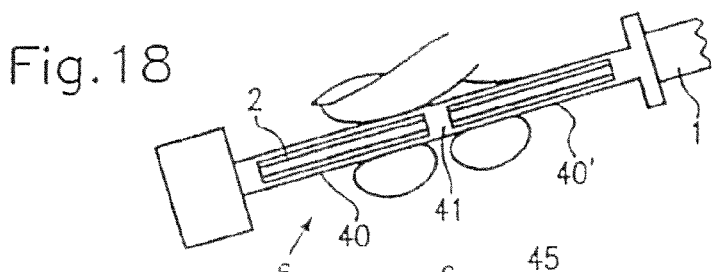
FIG. 18 shows the grip part from FIG. 17 in the extended position.

FIGS. 17 and 18 show an embodiment in which the grip part 6 has a deformable portion by means of which the distal end of the grip part, on which the protective element 3 lies, can be moved in the direction of the protection position on the needle tip by means of the deformable portion being deformed. In the illustrative embodiment according to FIGS. 17 and 18, two pairs of deformable brackets 40 and 40' are formed on the grip part 6 and these can be pressed together by the fingers so that they can be moved from the curved state in FIG. 17 to an extended state in FIG. 18. The two deformable pairs of brackets 40 and 40' are connected to one another by a sleeve portion 41. It is also possible to insert, between the two bracket pairs 40 and 40', an element which, when pressed by the fingers, changes the two deformable brackets 40 and 40 to the extended position according to FIG. 17.

Figure 19:
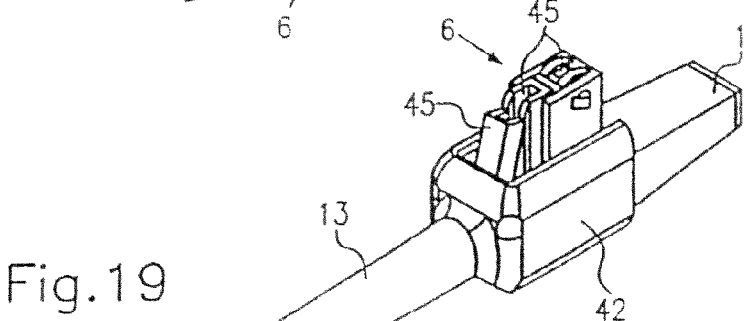
FIG. 19 shows a further embodiment of a deformable grip part in the starting position.
Figure 20:
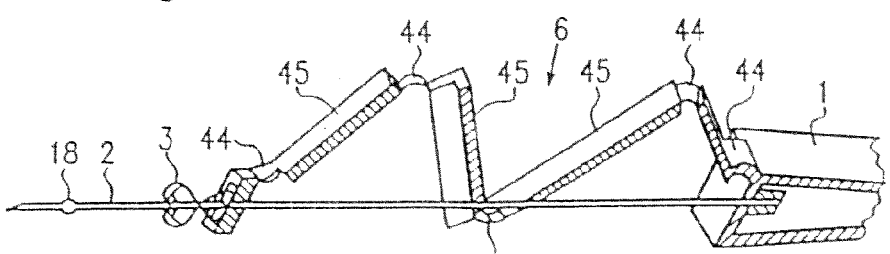
FIG. 20 shows the grip part from FIG. 19 in the deployed position.

FIGS. 19 and 20 show a further embodiment of a deformable grip part 6. FIG. 19 illustrating the grip part in the collapsed state in the standby position. The needle cap 13 is provided at the proximal end with a receiving portion 42 which receives collapsed portions 45 of the grip part 6, which is arranged between needle holder 1 and the protective element 3 (not shown in FIG. 19) arranged in the receiving portion 42.

FIG. 20 shows in schematic representation the grip part 6 in a partially deployed state after the needle cap 13 has been removed and an injection has been carried out. The stiff portions 45 of the grip part 6 which are connected to one another via articulations and hinge portions 44 and which are partially guided on the needle 2 are moved and aligned along the needle, the protective element 3 being pushed forward to the needle tip until it engages with the needle bulge 18 and covers the needle tip.

Compared to the embodiments according to FIGS. 17 through 20, the embodiments according to FIGS. 1 through 16 have the advantage that a greater cannula length is available in the standby position because the protective element 3 lies directly on the needle holder, whereas, in the embodiments according to FIGS. 17 through 20, a more complicated design of the grip part 6 is provided between protective element 3 and needle holder 1, as a result of which the available cannula length is restricted. The embodiment according to FIGS. 19 and 20 is also more advantageous in terms of the length of the available cannula than the embodiment according to FIGS. 17 and 18 because a more compact arrangement is made possible by the folding of the portions 45, as FIG. 19 shows when compared to FIG. 17. Instead of the fold portions in FIG. 20, a scissor mechanism between protective element and needle holder can also be provided in order to accommodate, in a smaller space, elements with which the protective element can be deployed.

Figure 14A:
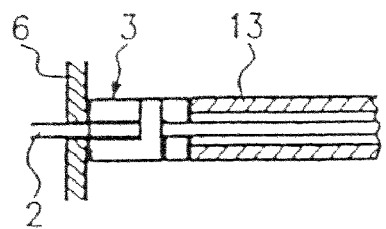

In all the embodiments, the protective element 3 is preferably a needle clip which is made of metal and whose intersecting arms issue from opposite sides of a proximal wall portion having a hole for the passage of the needle, the hole diameter being smaller than the maximum transverse dimension of the needle at the pinch 18, so that the needle clip is held in the protection position on the needle tip by means of the portion 18 of increased diameter. The intersecting arms extending on both sides of the needle 2, as FIG. 14a shows, have, at the distal end, an end portion which is widened to approximately the width of the rear wall and which, in the starting position, lies with elastic pretensioning on the outer circumference of the needle and, on reaching the needle tip, is moved by spring action into the protection position in which the two widened end portions engage over the needle tip. For this purpose, the distal ends of the arms, as the side views show, are slightly offset with respect to one another in the longitudinal direction or the arms are of different lengths, so that it is thus ensured that the two angled end portions of the arms engage over the needle tip. At least on the longer arm, the end portion is curved inward at the free edge in order to ensure that the needle tip is covered even if an attempt is made to push the needle clip back from the protection position on the needle, the inwardly curved end portion hooking onto the needle tip. The needle clip as a whole can be made very compact and only about 7 mm long.

Referring now to FIG. 21, a semi-schematic side view of an alternative safety Huber needle assembly 50 is shown comprising, a needle holder 52 and a middle retaining portion 54 received by the needle holder. The middle retaining portion 54 comprises a flange 31, which has a bore for receiving a Huber needle 2. An optional safety sleeve or Huber guard 56 made from a plastic material, such as a polyurethane material, is positioned over the Huber needle 2 to cover the needle tip 58 of the Huber needle. The Huber guard 56 comprises a central cylindrical section 60 and a pair of fins 62a, 62b extending from the central cylindrical section in opposing configuration.

As further discussed below, the Huber needle 2 is attached to a needle holding sleeve 64 of the needle holder 52, which has a lumen in fluid communication with the lumen of the Huber needle. In one exemplary embodiment, a medical grade plastic tubing 65 made from DEHP free PVC is attached at its first end 66 to an outlet end 103 (FIG. 22) of the needle holding sleeve 64 and at its second end 68 to a female Luer lock adapter 70. A screw cap 72 is threadedly engaged to the female Luer lock adapter 70 to preserve sterility until use. A tubing clamp 74, such as those offered by Halkey-Roberts of St. Petersburg, Fla., is disposed on the tubing 65 for isolating or clamping the tubing when desired.

FIG. 22 is a semi-schematic cross-sectional side view of the Huber needle assembly 50 of FIG. 21 from a reverse angle without the tubing 65 for clarity. As shown, the Huber needle 2 is attached to the needle holder 52 by means of a section of the needle proximal of a bent section 76 inserted into the inlet end 78 of the needle holding sleeve 64 and, in one embodiment, fixed in place by adhesive or glue. In the Huber needle ready to use position (FIGS. 21 and 22), at least a portion of the middle retaining portion 54 is received in the interior cavity 80 of the needle holder 52. In one exemplary embodiment, a tubular extension 82 of the middle retaining portion 54 extending from the base or flange 31 comprising an exterior surface 84 and an interior surface 86 extends into the interior cavity 80 of the needle holder 52. As further discussed below, the exterior surface 84 of the tubular extension 82 engages the surface of the interior cavity 80 of the needle holder 52 to maintain the two in removable engagement when in the ready to use position.

The interior surface 86 of the middle retaining portion 54 defines a retaining bore 88 adapted to pass the Huber needle 2 therethrough and to retain the protective element 3 therein. In one exemplary embodiment, this retaining configuration is implemented by incorporating a bump 85 comprising a reduced diameter section $D_r$ that is nominally smaller than an inside diameter dimension $D_{id}$ of the retaining bore 88, at either end or opening of the retaining bore. With reference to FIGS. 22 and 23, when the protective element 3 is in the ready to use position (FIGS. 22 and 23, top), the arms 92a, 92h (FIG. 23) are biased radially apart by the curved tips 94a, 94b abutting the side of the Huber needle 3. In this position, the dimension D2 measured from one intersecting joint 96a to another intersecting joint 96b is larger than the same measurement D1 measured when the arms 92a, 92b are in a relaxed state (i.e., not abutting the side of the needle) and the fingers 98a, 98b overlapped (FIG. 23, bottom). In one exemplary embodiment, the reduced diameter section $D_r$ is larger than D1 but is smaller than D2, which is smaller than $D_{id}$. Expressed mathematically, the diameters have the following relationship: $D1<D_r<D2<D_{id}$. Alternatively, D2 can be equal to $D_{id}$ or slightly larger than $D_{id}$ as the fingers 98a, 98b are able to flex when positioned inside the retaining bore 88 and slide past the bump 85.

The Huber needle assembly 50 may be placed in the ready to use position by first positioning the protective clip 3 over the Huber needle 2 and then sliding the Huber needle through the retaining bore 88 of the middle retaining portion 54. The Huber needle 2 may include a bulge or a crimp 91 for stopping the forward movement of the protective clip 3 when the opening 93 of the clip, which is smaller than the crimp 91, abuts the crimp. As the tubular extension 82 of the middle retaining portion 54 moves into the interior cavity 80 of the needle holder 52, the portions adjacent the interconnecting joints 96a, 96h of the protective clip 3 abuts the reduced diameter section $D_r$ of the retaining bore 88. Further downward movement of the needle holder 52 relative to the middle retaining portion 54 causes the protective clip 3 to flex and the fingers 98a, 98b move past the reduced diameter portion $D_r$ into the ready to use position. The relative movement stops when the upper end surface 100 of the middle retaining portion 54 abuts the interior surface of the interior cavity 80 of the needle holder 52.

FIG. 24 is a semi-schematic perspective view of the needle holder 52 without the Huber needle 2. The needle holder 52 comprises a central needle base structure 102 having the needle holding member 64 extending therefrom with an outlet 103. If the base 104 of the needle holder 52 defines a plane, preferably the needle holder member 64 extends at an angle relative to the plane, although not necessary (i.e., parallel to the plane). In one exemplary embodiment, the needle holder member 64 extends at about a 0 to about a 90 degree angle relative to the plane with 45 degrees being more preferred. The angled configuration facilitates running a tubing along a patient's skin, such as in the manner shown in FIG. 21.

A shroud 106 extends on each side of the central needle base structure 102 forming part of an enclosure or housing of the needle holder 52. In one exemplary embodiment, the shroud 106 comprises a plurality of gripping members 108 for facilitating gripping the needle holder 52, although a flat or smooth surface may also be incorporated. An optional pair of fins 110 may be incorporated in the needle holder 52, one fin over each shroud 106. A pair of ledges 111 (FIGS. 25 and 26) extend from the base of the shrouds 106 and of the fins for added reinforcement, although not required. In one exemplary embodiment, the shrouds 106 can have an upper surface 112 (FIG. 24) that is generally flushed or even with the upper surface 114 of the central needle base structure 102. Accordingly, many alterations may be made to the structure and features of the needle holder 52 without deviating from the spirit and scope of the present invention.

A gap or channel 116 is provided intermediate the two shrouds 106. The channel 116 runs or extends a portion of the top surface of the needle holder 52 and the entire length of the front side opposite the central needle base structure 102. For assembling or making the needle holder 52, the channel 116 facilitates insertion of the blunt end of the Huber needle 2 into the inlet end 78 of the needle holding member 64 as the gap defined by the channel provides access into the interior cavity 80 of the needle holder 52. Alternatively, the channel 116 can extend a portion of the length of the front side opposite the central needle base structure 102 and a portion of the top surface of the needle holder 52 and still provide for access to the interior cavity 80 for mounting the Huber needle 2.

FIG. 25 is a semi-schematic cross-sectional side view of the needle holder 52 of FIG. 24 taken along a lengthwise direction. The interior cavity 80 of the needle holder 52 comprises a main interior section 118, a secondary interior section 120, and a secondary slot 122 adjacent the main interior section 118, which forms part of the channel 116. As further discussed below, the main interior section 118 is configured to receive the tubular extension 82 of the middle retaining portion 54 and either one of the secondary interior section 120 or secondary slot 122 is configured to receive an orientation marker 124 (FIG. 27) to angularly align the middle retaining portion 54 to the needle holder 52.

An inwardly extending protrusion 126 is incorporated on each interior surface of each shroud 104. The inwardly extending protrusion 126 may comprise a single continuous anchor or projection extending along at least a portion of the interior surface of the shroud 104 at the main interior section 118 or may alternatively comprise two or more individual anchors on the interior surface of each shroud 106. The inwardly extending protrusion 126 is configured to snap or mate with a groove 128 (FIG. 27) on the tubular extension 82 to removably secure the middle retaining portion 54 to the interior cavity 80 of the needle holder 52 in a detent-type engagement when in the ready position.

FIG. 26 is a semi-schematic bottom view of the needle holder 52 of FIG. 24. In the configuration shown, the main interior section 118 of the interior cavity 80 is semi-frusto-conical in shape, in view of the gaps 120, 122, with the interior surface 130 of the main interior section 118 having a slight taper that tapers inwardly from about the base 104 towards the top 105. However, a straight wall surface without a slight taper may be incorporated. Side wall portions 132 of the central needle base structure 102 extend at an angle from the back wall 134 of the central needle base structure 102 to create a generally rectangular secondary interior section 120 of the interior cavity 80. However, this secondary interior section 120 may incorporate other configurations by changing the contour or shape of the side wall portions, such as a square or a curved structure.

FIG. 27 is a semi-schematic cross-sectional side view of the middle retaining portion 54 provided in accordance with aspects of the present invention. In the figure shown, the orientation marker 124 is attached to the tubular extension 82 via a webbing 136, which is similar to a rib and, in one embodiment, is integrally molded with the flange 31, the orientation marker 124, and the tubular extension 82. The orientation marker 124 is configured to fit into the secondary interior section 120 of the interior cavity 80 or the secondary slot 122 when the middle retaining portion 54 is removably mated to the needle holder 52. The middle retaining portion 54 may be made from polyethylene or similar plastics and may be enhanced with color, such as a light green or other desired colors. A plurality of openings (not shown) may be incorporated in the base 31 of the middle retaining portion 54 to facilitate taping the base to the patient. The openings can vary in shapes, sizes, and numbers and can also be eliminated.

Referring now to FIG. 28 in addition to FIG. 22, the alternative needle assembly 50 may be used by first removing the safety sleeve 56 from the Huber needle 2. The needle 2 is then inserted into a subject until the flange 31 abuts the subject. When the injection is completed, the needle 2 may be withdrawn from the subject and the needle tip shielded by the protective clip 3 by holding onto the flange 31 while concurrently retracting the needle 2 proximally or away from the subject. During this proximal needle motion, the intersecting joints 96a, 96b of the needle clip 3 abut the reduced diameter section $D_r$ of the main internal section 118 of the interior cavity 80 of the middle retaining portion 54 to permit the needle to move relative to the protective clip 3. As previously discussed, this relative movement is provided due to the larger clip dimension D2 (FIG. 23) when the curved lips 94a, 94b of the needle clip 3 abut the side of the needle 2 as compared to the reduced diameter section $D_r$ of the interior cavity 80.

When the needle tip moves proximal of the curved lips 94a, 94b of the needle clip 3 so that the needle clip 3 is no longer biased by the needle (FIGS. 23, bottom, and 28), the resilient arms 92a, 92b are unrestrained and flex radially inwardly over the needle tip. This radial movement causes the measurement of the two intersecting joints 96a, 96b (FIG. 23) to decrease from D2 to D1 while at the same time allows the fingers 98a, 98b to overlap over the needle tip to shield the needle tip. As the measurement D1 between the two intersecting joints 96a, 96b is now smaller than the reduced diameter section $D_r$ of the interior cavity 80, the needle clip 3 is able to slip past the reduced diameter section $D_r$ of the bore 88 when the needle 2 is further moved proximally (FIG. 28). The needle clip 3 is now attached to the needle 2 and separates from the middle retaining portion 54 (FIG. 28).

Figure 29:
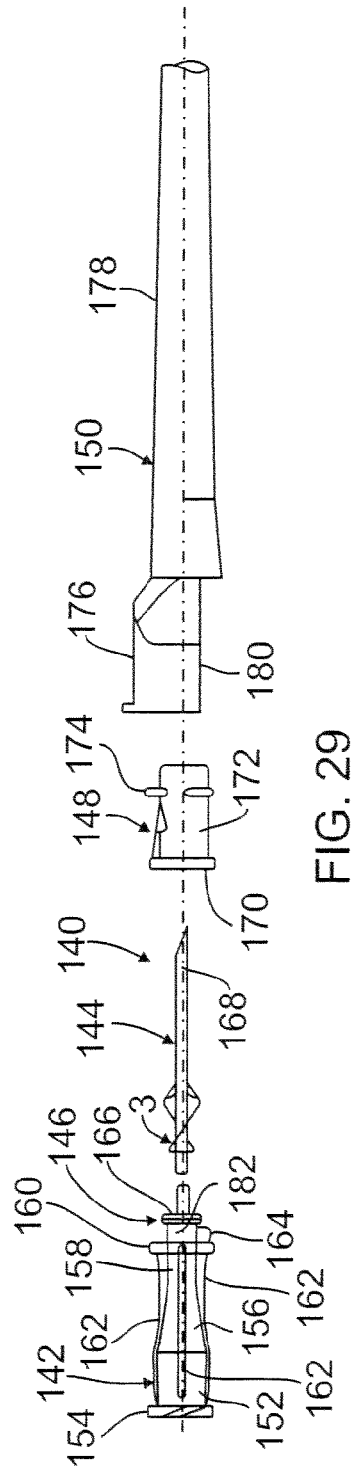
FIG. 29 is a semi-schematic exploded side view of yet another alternative needle assembly provided in accordance with aspects of the present invention.
Figure 30:
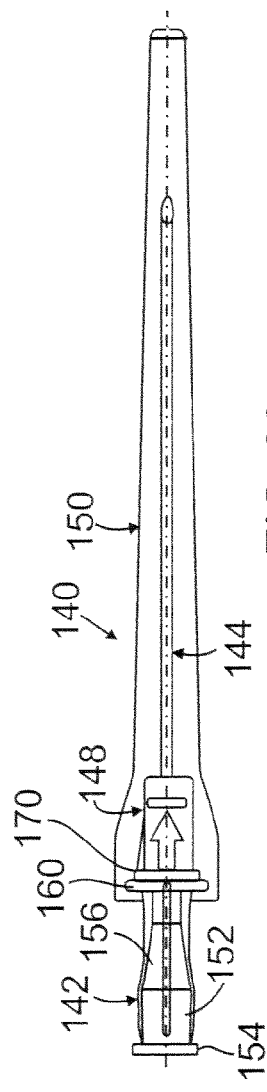
FIG. 30 is a semi-schematic side view of the needle assembly of FIG. 29 in an assembled state.
Figure 31:
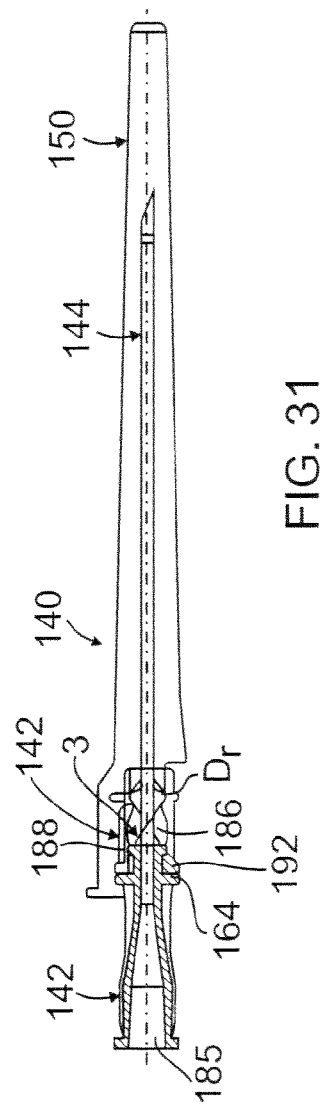
FIG. 31 is a semi-schematic cross-sectional side view of the needle assembly of FIG. 30.

FIGS. 29-31 show another alternative needle assembly 140 provided in accordance with aspects of the present invention in various views and state of assembly. Referring initially to FIG. 29, the needle assembly 140 comprises a needle hub 142, a needle 144 having a protective clip 3 positioned thereon attached at its proximal end to the distal end 146 of the needle hub 142, a middle retaining portion 148, and a needle cover 150. The needle hub 142 comprises a base section 152 having a Luer lock 154 and a transition section 156 that connects to a nose section 158 having a nose flange 160 positioned thereon. A plurality of spaced apart ribs 162 are formed along the exterior surface of the hub, which in one exemplary embodiment comprises four ribs evenly spaced along the exterior surface although no ribs, fewer ribs, or more ribs may be included without deviating from the spirit and scope of the present invention.

The nose section 158 further comprises an alignment plate 164, which in one exemplary embodiment is an extension of one of the ribs distal of the nose flange 160. The alignment plate 164 cooperates with a notch on the middle retaining portion 148 to angularly align the middle retaining portion to the needle hub 142, as further discussed below. An end flange 166 is incorporated at the distal end 146 of the nose section 158 having a diameter larger than the diameter of the nose section 158. Preferably the diameter of the end flange 166 is approximately the same as the inside diameter of the middle retaining portion 148 for size-on-size or frictional engagement with the inside diameter of the middle retaining portion (FIG. 31). Alternatively, the end flange 166 may be eliminated and the nose section 158 sized to form a size-on-size or friction fit with the interior surface of the middle retaining portion 148. Still in another alternative embodiment, the fit between the middle retaining portion 148 and the end flange 166 or the nose section 158 is a slight loose fit for easy operability of the middle retaining portion from a ready to use position to an activated position.

The needle clip 3, which is the same as the needle clip described above (See, e.g., is positioned on the needle 144. The needle clip 3 is configured to move from a proximal position on the needle 144 to a distal position on the needle to block the needle tip, as further discussed below. In one exemplary embodiment, a crimp or bump 168 is incorporated near the needle tip to stop the distal movement of the needle clip 3. However, a clip that frictionally engages with the needle shaft in the absence of the crimp or bump may also be used with the present needle assembly, as well as other needle assemblies described elsewhere herein.

The middle retaining portion 148 is configured to retain the needle clip 3 at the proximal end of the needle when in a ready to use position (FIGS. 30 and 31) and move the needle clip to a blocking position when activated. In one exemplary embodiment, the middle retaining portion 148 comprises a rear flange 170, a tubular body 172, which may include a generally tapering cylinder or other shaped bodies, and a gripping flange 174. In one exemplary embodiment, the gripping flange 172 comprises two separate upper and lower projections. However, a continuous circular flange, a continuous square flange, other shaped flanges, or no flange may be incorporated. The gripping flange 174 facilitates gripping by a user in moving the middle retaining portion 148 distally to activate the protective clip 3 over the needle tip.

The needle cover 150 comprises a base section 176 and a protective section 178. The base section 176 is configured to removably engage with the nose flange 160 on the needle hub 142 while the protective section 178 is configured to shield the needle and needle tip prior to usage of the needle. In one exemplary embodiment, the base section 176 comprises an opened lower section 180 and a pair of grooves or detents on an inside interior surface (not shown) of the base section 176. The pair of grooves or detents are configured to latch with the nose flange 160 in a detent-type configuration. In one exemplary embodiment, the needle cover 150 is semi-opaque to permit visual inspection of the needle prior to use.

Referring now to FIG. 30 in addition to FIG. 29, in a ready to use position, the middle retaining portion 148 is telescopically positioned over the nose tip section 182 of the nose section 158. Although the rear flange 170 of the middle retaining portion 148 is shown abut the nose flange 160 of the nose section 158, a slight gap or space is acceptable provided the positioning of the middle retaining portion 148 over the nose section allows the protective clip 3 to slide over a projection or bump inside the middle retaining portion, as further discussed below.

An indicia 184, such as an arrow or a marker, may be incorporated on the middle retaining portion 148 for either aesthetic reasons or for conferring instructions to a user to advance the middle retaining portion in the direction indicated, or both. However, the indicia 184 may be eliminated as the use of the needle assembly 140 is intuitive without the indicia.

FIG. 31 is a cross-sectional side view of the needle assembly of FIG. 30 from a different viewing angle. As shown, the middle retaining portion 142 comprises a bore 186 having an interior surface that includes bump or a reduced diameter section $D_r$ similar in configuration as the middle retaining portion 54 of FIGS. 27 and 28. The bump or reduced diameter section $D_r$ of FIG. 31 cooperates with the protective clip 3 in the same way as the middle retaining portion 54 and needle clip 3 of FIGS. 23-28 to provide the same retaining and relative movement functions. Also shown is a needle hub bore 185, which is configured to receive a Luer tip of a syringe (not shown) or other medical implements.

The protective clip 3 may be moved to a ready to use position by pushing the middle retaining portion 148 over the nose tip section 182 of the needle hub 142. To ensure that the distal portion of the protective clip 3 (See, e.g., the portions comprising the intersecting joints 96a, 96b of FIG. 23) slides past the bump or reduced diameter section $D_r$ of the middle retaining portion 148, the distance between the reduced diameter section $D_r$ and the distal end surface 188 of the nose section 158 of the needle hub 142 should be less than the distance between the proximal end wall 190 of the protective clip 3 and the intersection joints 96a, 96b of the protective clip 3 (See, e.g., FIG. 23). Once mounted in the position shown (FIG. 31), the protective clip 3 moves with the middle retaining portion 148 and relative to the needle 3 until the clip is no longer urged by the needle, as further described below and as described above with reference to FIGS. 22 and 28.

A slot or notch 192 is incorporated at the proximal end of the middle retaining portion 142. The notch 192 is configured to receive the alignment plate 164 on the nose section 158 of the needle hub 142 to angularly align the middle retaining portion 148 to the needle hub 142. However, the notch 192 and the alignment plate 164 may be eliminated if angular alignment between the needle huh 142 and the middle retaining portion 142 is not necessary.

The needle assembly 140 may be used by first mounting the needle hub 142 over a syringe or other medical implement and then removing the needle cover 150. A fluid may be aspirated into the syringe via the needle or the needle may be inserted into a subject if a fluid sample from the subject is to be taken. Following the injection, the needle 144 is retracted or withdrawn from the subject (either by pulling on the syringe (not shown) or grapping the needle hub 142 and pulling on the needle hub away from the subject) with one hand while holding or grabbing onto the middle retaining portion 148 with the other hand.

As the needle is retracted, the protective clip 3 is held by the reduced diameter section $D_r$ of the middle retaining portion 148 and moves relative to the needle 144 until the needle tip moves proximal of the curved lips 94a, 94b (See. FIG. 23, bottom), at which point the protective clip moves radially inwardly such that the fingers 98a, 98b overlap over the needle tip to shield the needle tip. Approximately simultaneously therewith, the cross-sectional dimension of the protective clip 3 at its distal end collapses or reduces in size so that said section of the protective clip is now smaller than the reduced diameter section $D_r$ of the middle retaining portion 148, which then allows the protective clip 3 to separate from the middle retaining portion. The needle and needle hub may then be disposed of pursuant to standard protocols.

Although limited embodiments of the syringe assemblies and their components have been specifically described and illustrated herein, many modifications and variations will be apparent to those skilled in the art. Accordingly, it is to be understood that the syringe assemblies and their components constructed according to principles of this invention may be embodied other than as specifically described herein. The invention is defined in the following claims.

The invention claimed is:

1. A needle assembly comprising:
a needle having a needle shaft and a needle tip attached to a needle holder at a proximal end of the needle shaft;
a protective element movably positioned on the needle shaft for protecting the needle tip, said protective element comprising a proximal wall having an outer dimension and an opening and two arms;
a grip part provided between the protective element and the needle holder for containing and moving the protective element from a proximal position on the needle shaft to a distal position on the needle shaft, the grip part comprising a wall located proximally of the protective element and having an opening for sliding about the needle shaft, and wherein the opening comprises a diameter of a first dimension, which is smaller than the outer dimension on the proximal wall of the protective element; and
wherein the two arms cross the needle shaft when viewed from a side of the needle shaft in a ready position; the protective element further comprising a distal end portion that lies to the side of the needle shaft and, on reaching the needle tip, is movable by spring action over the needle tip into a protection position, and wherein the ready position is characterized by the needle tip being exposed for an injection or an infusion.

2. The needle assembly of claim 1, whereby the grip part is prevented from being removed from the needle.

3. The needle assembly of claim 1, wherein the protective element comprises a sleeve having a generally cylindrical body for interacting with the needle tip to prevent the protective element from being removed from the needle.

4. The needle assembly of claim 1, wherein the protective element is made from a metal material.

5. The needle assembly of claim 1, wherein the two intersecting arms are of dissimilar lengths.

6. The needle assembly of claim 1, wherein the grip comprises a cylindrical side wall for substantially covering a length of the protective element.

7. The needle assembly of claim 1, wherein the grip part has a side wall that substantially surrounds the protective element.

8. A needle assembly comprising:
a needle having a needle shaft defining a needle axis and a needle tip attached to a needle holder at a proximal end of the needle shaft;
a grip part with a grippable surface slidably mounted on the needle shaft; the grip part comprising a cylindrical wall section defining an interior cavity and a wall having an opening therein for sliding about the needle shaft;
a protective element comprising a proximal wall having an outer dimension and an opening slidably positioned on the needle shaft and inside the interior cavity of the cylindrical wall section; the protective element comprising two arms extending distally of the proximal wall and each crossing the needle axis when in a ready position such that each arm comprising an arm section located on one side of the needle shaft and another arm section located on an opposite side of the needle shaft; the ready position is characterized by the needle tip being exposed for an injection or an infusion;
wherein the opening on the grip part comprises a diameter of a first dimension, which is smaller than the outer dimension on the proximal wall of the protective element.

9. The needle assembly of claim 8, wherein the needle tip comprises a bend.

10. The needle assembly of claim 8, whereby the grip part is prevented from being removed from the needle by the protective element.

11. The needle assembly of claim 8, further comprising a sleeve having a generally cylindrical body for interacting with an enlarged diameter section of the needle shaft to prevent the protective element from being removed from the needle.

12. The needle assembly of claim 8, wherein the protective element is made from a metal material.

13. The needle assembly of claim 8, wherein the opening on the wall of the grip part has a dimension measured along a diameter of the opening, and the proximal wall of the protective element has a dimension measured along two opposing edges of the proximal wall; and wherein the dimension of the opening of the grip part is smaller than the dimension of the proximal wall.

14. The needle assembly of claim 8, further comprising a plurality of ribs formed on an exterior surface of the grip part.

15. The needle assembly of claim 8, further comprising an opening on a distal end of the grip part.

* * * * *

UNITED STATES PATENT AND TRADEMARK OFFICE
CERTIFICATE OF CORRECTION

PATENT NO.       : 8,376,994 B2
APPLICATION NO.  : 13/099945
DATED            : February 19, 2013
INVENTOR(S)      : Woehr et al.

It is certified that error appears in the above-identified patent and that said Letters Patent is hereby corrected as shown below:

On the Title Page

On page 1, column 1, line 4, Inventors, delete "Danielsvile," and insert -- Danielsville, --, therefor.

On page 1, References Cited, column 2, line 4, Other Publications, delete "Melsunqen" and insert -- Melsungen --, therefor.

On page 2, References Cited, column 2, line 29, Other Publications, delete "Advisor" and insert -- Advisory --, therefor.

On page 2, References Cited, column 2, line 50, Other Publications, delete "7,264,61." and insert -- 7,264,613. --, therefor.

On page 3, References Cited, column 1, line 47, Other Publications, delete "Klingseisen." and insert -- Klingseisen, --, therefor.

On page 3, References Cited, column 1, line 60, Other Publications, delete "ASD" and insert -- ASD, --, therefor.

On page 3, References Cited, column 2, line 16, Other Publications, delete "VVoehr;" and insert -- Woehr; --, therefor.

On page 3, References Cited, column 2, line 39, Other Publications, delete "(Third Ressondent)" and insert -- (Third Respondent) --, therefor.

On page 3, References Cited, column 2, line 40, Other Publications, delete "Paten" and insert -- Patent --, therefor.

On page 3, References Cited, column 2, line 70, Other Publications, delete "Leonardos& CIA" and insert -- Leonardos & CIA --, therefor.

Signed and Sealed this
Fourth Day of November, 2014

Michelle K. Lee
*Deputy Director of the United States Patent and Trademark Office*

CERTIFICATE OF CORRECTION (continued)
U.S. Pat. No. 8,376,994 B2

On page 3, References Cited, column 2, line 73, Other Publications, after "AG," insert -- Classification: A61 M 25/06; A61 M 5/32, --.

On page 4, References Cited, column 1, line 6, Other Publications, delete "PI0812128-6," and insert -- PIP812128-6, --, therefor.

On page 4, References Cited, column 1, line 15, Other Publications, delete "No. 5, 5,504," and insert -- No. 5,135,504, --, therefor.

On page 4, References Cited, column 1, line 26, Other Publications, delete "includin" and insert -- including --, therefor.

On page 4, References Cited, column 2, line 35, Other Publications, delete "Attachment a" and insert -- Attachment A --, therefor In the Specification Column 3, line 17, after "according" insert -- to --.

Column 3, line 62, delete "form" and insert -- from --, therefor.

Column 5, line 16, delete "rip" and insert -- grip --, therefor.

Column 5, line 25, delete "of" and insert -- of the --, therefor.

Column 6, line 43, delete "part 25" and insert -- part 25' --, therefor.

Column 6, line 47, delete "huh" and insert -- hub --, therefor.

Column 7, line 6, delete "hearing" and insert -- bearing --, therefor.

Column 7, line 57, delete "1'" and insert -- 1'. --, therefor.

Column 8, line 38, delete "40 to" and insert -- 40' to --, therefor.

Column 9, lines 35-36, delete "comprising," and insert -- comprising --, therefor.

Column 10, line 18, delete "92h" and insert -- 92b --, therefor.

Column 10, line 43, delete "96h" and insert -- 96b --, therefor.

Column 13, line 18, delete "(See, e.g.," and insert -- (See, e.g., FIG. 23), --, therefor.

Column 14, line 8, delete "$D_r$" and insert -- $D_r$, --, therefor.

Column 14, line 38, delete "huh" and insert -- hub --, therefor.

Column 14, line 54, delete "(See." and insert -- (See, --, therefor.